(12) United States Patent
Bardetsky et al.

(10) Patent No.: US 6,449,580 B1
(45) Date of Patent: Sep. 10, 2002

(54) EVALUATING PROPERTIES OF OIL USING DIELECTRIC SPECTROSCOPY

(75) Inventors: Alexander Bardetsky, Cincinnati, OH (US); Vladimir Brovkov, Odessa (UA)

(73) Assignee: Entek IRD International Corporation, Milford, OH (US)

( * ) Notice: Subject to any disclaimer, the term of this patent is extended or adjusted under 35 U.S.C. 154(b) by 0 days.

(21) Appl. No.: 09/075,622

(22) Filed: May 11, 1998

(51) Int. Cl.$^7$ .................. G01K 13/00; G01K 17/00
(52) U.S. Cl. ................ 702/130; 702/127; 702/136; 702/137; 73/32 R
(58) Field of Search ................. 702/50, 52, 81–84, 702/100, 113, 114, 130, 136, 137; 73/1.02, 32 R, 54.01, 54.02, 53.05, 54.42; 340/603; 324/204, 553, 663, 664, 670, 685

(56) References Cited

U.S. PATENT DOCUMENTS 3,478,589 A * 11/1969 Birken .................. 374/184

(List continued on next page.)

FOREIGN PATENT DOCUMENTS

| DK | 3402708 A1 | * 8/1985 |
| EP | 0377974 A2 | * 7/1990 |
| GB | 2306660 | 5/1997 |
| GB | 2306660 A | * 7/1997 |
| JP | 411257042 A | * 9/1999 |
| SU | 0987471 | 1/1983 |
| SU | 1401377 | 6/1988 |
| SU | 1555655 | 4/1990 |
| SU | 1566291 | 5/1990 |
| SU | 1566291 A | * 5/1990 |
| SU | 1758507 | 8/1992 |
| UA | 9408672 | 11/1996 |

OTHER PUBLICATIONS

Abstract, Laboratory determine of lubricant–quality–by heating till maximum value of tangent of dielectric loss angle is attained., Soviet Union Patent No. 1566291, May 23, 1990.

(List continued on next page.)

Primary Examiner—Marc S. Hoff
Assistant Examiner—Manuel L. Barbee
(74) Attorney, Agent, or Firm—Wood, Herron & Evans, L.L.P.

(57) ABSTRACT

A working fluid of a mechanical system is analyzed by measuring the permittivity of the working fluid as the temperature of the working fluid is varied over a range. Within this temperature range, a special temperature is identified, at which the rate of change of the permittivity over temperature is at a maximum. Subsequently, the viscosity, acid content, moisture content and density of the working fluid are determined from the special temperature, rate of change of permittivity at the special temperature, permittivity of the special temperature, and rate of change of permittivity above the special temperature, respectively. To ensure accurate determination of the special temperature and other parameter values, a curve-fitting technique is used, in which measurements of permittivity over the temperature range are fitted to a mathematical model of the expected curve, and this mathematical model is used to identify the various parameter values. Apparatus for performing this analysis method may be in the form of a desk-top oil analyzer for use in an on-site application, or an integrated analysis device suitable for mounting directly to the mechanical system, e.g., in the form of an adapter insertable between the oil filter and oil filter mounting. The working fluid being analyzed may be oil, hydraulic fluid, or any other fluid used in a mechanical system which is subject to contamination and degradation.

105 Claims, 12 Drawing Sheets

U.S. PATENT DOCUMENTS

| | | | | |
|---|---|---|---|---|
| 3,933,030 | A | * | 1/1976 | Forster et al. ............... 73/32 R |
| 4,165,633 | A | * | 8/1979 | Faisanen ........................ 73/76 |
| 4,646,070 | A | | 2/1987 | Yasuhara et al. ............ 340/603 |
| 4,733,556 | A | | 3/1988 | Metizler et al. ............ 73/53.05 |
| 4,932,243 | A | * | 6/1990 | Suh et al. ........................ 73/73 |
| 5,262,732 | A | | 11/1993 | Dickert et al. ............... 324/672 |
| 5,334,941 | A | * | 8/1994 | King ........................... 324/637 |
| 5,394,739 | A | | 3/1995 | Garvey, III et al. ........ 73/54.23 |
| 5,506,501 | A | | 4/1996 | Fogel et al. ................. 324/204 |
| 5,614,830 | A | | 3/1997 | Dickert et al. ............... 324/553 |
| 5,644,239 | A | * | 7/1997 | Huang et al. ................ 324/439 |
| 5,656,767 | A | | 8/1997 | Garvey, III et al. ......... 540/540 |
| 5,674,401 | A | | 10/1997 | Dickert et al. ............... 210/695 |

OTHER PUBLICATIONS

Abstract, Wear product content in lubricant monitoring device–has bellows to react to weight of wear products in lubricant, while capillary tube is used to determine level of indicating liquid depending on weight., Soviet Union Patent No. 1758507, Aug. 30, 1992.

Abstract, Metal dust concentration in lubricants detector–has electromagnetic filter in supply channel input coupled to clock pulses generator., Soviet Union Patent No. 987471, Jan. 7, 1983.

Abstract, Wear product in lubricant sensor–has two perforated electrodes to form electric field to concentrate wear products and dielectric losses are recorded., Soviet Union Patent No. 1401377, Jun. 7, 1988.

Brown et al., Novel Sensors for Portable Oil Analyzer, JOAP International Condition Monitoring Conference (1998) 91–100.

Carey, The Dielectric Constant of Lubrication Oils, JOAP International Condition Monitoring Conference (1998) 423–431.

Abstract, Liquid dielectric water content determing unit–traces calibration curves of dielectric losses angle tangent for given temperature range., Soviet Union Patent No. 1555655, Apr. 7, 1990.

American Society for Testing and Materials, Standard Test Method for Kinematic Viscosity of Transparent and Opaque Liquids, Designation: D445–01, 71/1/97; 2001.

American Society for Testing and Materials, Standard Test Method for Acid Number of Petroleum Products by Potentiometric Titration, Designation: D664–95 (Reapproved 2001), 177/96; 1995.

American Society for Testing and Materials, Standard Test Method for Water in Petroleum Products and Bituminous Materials by Distillation, Designation: D95–99, 74/82 (88); MPMS Chapter 10.5, 1999.

* cited by examiner

Derivative of the $\varepsilon = f(t)$ function in the Special Temperature Point, $d\varepsilon/dt_{STP}$ Dielectric constant @ Special Temperature Point

EVALUATING PROPERTIES OF OIL USING DIELECTRIC SPECTROSCOPY

FIELD OF THE INVENTION

The present invention relates to evaluation of properties of fluids used in mechanical systems, such as lubricating oil and hydraulic fluid, including water content, viscosity, acid content and density of the fluid.

BACKGROUND OF THE INVENTION

Mineral and synthetic working fluids, such as motor oil, gear oil and hydraulic liquids, are frequently used essential components of mechanical systems. Working fluids provide lubrication and/or force and energy transfer in the mechanical system. Unfortunately, working fluids are subject to degradation with use over time. For example, working fluids may be contaminated by water or debris. In addition, contamination of working fluids by water and dissolved air leads to accumulation of oxide products, increasing the fluid viscosity and reducing its lubricating effect. Such contamination and degradation leads to increased friction in the mechanical system and ultimately to premature failure due to wear.

In many industrial environments, working fluids are regularly analyzed to determine if fluid breakdown is occurring, threatening mechanical failure. Laboratory methods for detecting working fluid viscosity and degradation are described in ASTM standards D445-94 entitled Kinematic Viscosity of Transparent and Opaque Liquids (the Calculation of Dynamic Viscosity), D95-83 (1990) entitled Water in Petroleum Products and Bituminous Materials by Distillation and D664-95 entitled Acid Number of Petroleum Products by Potentiometric Titration.

Unfortunately, accurate oil analysis typically requires shipment of a fluid sample to a laboratory for analysis. This results in latency between the sampling of the working fluid and the generation of analysis results. This problem is particularly vexing where the mechanical system is in a moving vehicle such as a ship or aircraft, or is located in a rural area such as a factory.

Unfortunately, these laboratory methods have major weaknesses. First, laboratory analysis has a significant cost, and typically cannot be performed on-site. Furthermore, if a working fluid sample must be transported off-site for analysis, a significant delay will occur between sampling and receipt of the test results. A relatively simple method for working fluid analysis which does not require extensive laboratory equipment and can be performed on-site without expertise, would clearly be preferable. Ideally, the simplicity of the method would permit an analyzing device for evaluating the working fluid, to be incorporated into the mechanical system, so that analysis of oil in the system is performed continuously while the system is on-line, i.e., still operating. Such an approach would eliminate all unnecessary downtime, because the system could be operated continuously until the oil is found to need replacement, and the replacement can be made immediately rather than after an oil sample has been delivered to a laboratory and analyzed. Furthermore, in automotive applications, an on-line oil analysis method that identifies when oil should be changed, could in many instances lead to greater mileage between oil changes reducing maintenance costs, environmental strain caused by disposal of waste oil, and inconvenience.

Several proposals have been made for performing on-site or on-line analysis of working fluid using relatively simple analyzing devices. One popular proposal involves measuring dielectric properties of the working fluid and implying properties of the working fluid from the results. For example, U.S. Pat. No. 4,646,070 describes a sensor including a pair of electrodes which are placed in an oil-carrying passage of the mechanical system, and immersed in the flowing oil to form a capacitor. The capacitance of this capacitor varies as a function of the permittivity of the oil. A measuring circuit determines the permittivity of the oil and generates a measure of the quality of the oil. U.S. Pat. No. 4,733,556 describes a sensor with two pairs of capacitive electrodes. The first pair of electrodes is immersed in oil flowing in the operating mechanical system, and a second pair of electrodes is immersed in reference oil. A circuit compares the capacitance measured from the two pairs of electrodes, and produces a measure of the quality of the oil. Other sensors measure the variation of the permittivity of oil over frequency, and use the resulting data to determine a measure of the quality of the oil.

Unfortunately, these proposed systems have not been widely accepted for measurement of oil parameters. The permittivity of a working fluid such as oil depends on a large number of independent parameters. For example, the concentration of oxidized molecules (acid content), water content, particulate content, viscosity and temperature of oil all influence the permittivity of oil and its variation over frequency. Thus, a measurement of permittivity per se or the variation of the permittivity over frequency will not determine a value for any one of these parameters independent of the others. However, to adequately characterize the performance of a working fluid and determine whether the working fluid should be replaced, all of the parameters of water content, acid content, viscosity and density, need to be independently and accurately measured, and then evaluated separately. The quality measurements produced by the systems described in the above patents, are dependent upon several different oil parameters, and thus cannot be related to any one parameter or easily used to answer the basic question of whether oil should be replaced.

Soviet patent 1,566,291, authored by an inventor of this application, describes a method for analyzing the properties of oil based on variation of dielectric parameters of the oil over temperature. This method produces measurements of parameters of oil that are independent of most other parameters. In this method, a capacitive-type sensor is immersed in the oil, and a circuit stimulates the sensor to determine the dielectric loss in the capacitive sensor. The dielectric loss of the oil (which results from the imaginary part of the complex function for permittivity) varies non-linearly with temperature. In accordance with the method of the Soviet '291 patent, the oil is heated while monitoring the change in the dielectric loss. The ratio of the imaginary to the real part of the permittivity is known as tangent delta or tgδ. At the oil's "critical temperature", tgδ reaches a maximum value. This critical temperature is identified by monitoring tgδ as the oil temperature is increased, and identifying the temperature at which tgδ ceases increasing and begins decreasing. The determined value of the critical temperature is converted to a measure of the viscosity of the oil, using a calibrated plot shown in FIG. 4. The determined maximum value of tgδ is converted into a measure of the acid content of the oil using a calibrated plot shown in FIG. 5.

Unfortunately, the method described in the Soviet '291 patent is flawed in several ways. First, the described method for locating the critical temperature is not accurate. Measurement variations can produce an apparent decrease in tgδ, incorrectly suggesting that the critical temperature has been located, resulting in a mis-determination of the critical temperature and mis-determination of the oil viscosity. Furthermore, the value of tgδ at the critical temperature is not only related to the acid content of the oil, it is also related to the water content of the oil. Accordingly, in the described method, variation in water content of the oil can lead to an incorrect measurement of acid content.

Accordingly, there remains a need for a method for measuring parameters of oil including viscosity, density, acid content and water content, independently of other parameters, which is accurate and requires relatively simple analyzing devices suitable for on-site or on-line applications.

SUMMARY OF THE INVENTION

The present invention provides a method and apparatus for analyzing working fluid which meets these objectives. In the embodiment described below, the permittivity of the working fluid is measured as the temperature of the working fluid is varied over a range, which range includes a special temperature where the rate of change of the permittivity over temperature is at a maximum. Subsequently, various parameters of the working fluid can be determined.

In one aspect of the present invention, the value of the special temperature is directly converted to a measure of viscosity of the working fluid, using an appropriately generated plot of viscosity relative to special temperature.

In a second aspect of the present invention, the rate of change of the permittivity with respect to temperature is directly converted to a measure of the acid content of the working fluid, using an appropriately generated plot of acid number relative to the rate of change of the permittivity at the special temperature.

In a third aspect of the present invention, the value of the permittivity of the working fluid at the special temperature is directly converted to a measure of the moisture content of the working fluid, using an appropriately generated plot of moisture content relative to the value of the permittivity at the special temperature.

In a fourth aspect of the present invention, the rate of change of the permittivity of the working fluid with respect to temperature, below the special temperature, is directly converted to a measure of the density of the working fluid, using an expression relating working fluid density relative to the rate of change of the permittivity below the special temperature.

In a further aspect, a working fluid attribute is determined accurately by a curve-fitting technique. Measurements of a working fluid parameter (in the above aspects, this parameter is the fluid's permittivity) are taken over a variation in an environmental variable (in the above aspects, this variable is temperature). The measurements are then fitted to a mathematical model of the expected curve of the variation in the working fluid parameter over variation in the environmental variable. Finally, this mathematical model is analyzed to identify an attribute of the working fluid.

In the embodiment described below, this curve-fitting technique is used to form a mathematical model of the curve of the variation in the permittivity over temperature. Then, the special temperature is identified by locating the temperature at which there is an inflection point in the model curve, and this temperature is used to identify the viscosity of the working fluid. Further, the mathematical model is used to compute the rate of change of the permittivity with respect to temperature, and this rate of change is used to identify the acid content of the working fluid. Also, the mathematical model is used to compute the value of the permittivity of the working fluid at the special temperature, and this value is used to identify the moisture content of the working fluid. Finally, the mathematical model is used to identify the rate of change of the permittivity of the working fluid with respect to temperature, below the special temperature, and this value is used to identify the working fluid density.

In each of the above embodiments, the working fluid may be oil, hydraulic fluid, or any other fluid used in a mechanical system which is subject to contamination and degradation. Furthermore, principles of the present invention could also be applied to analysis of other hydrocarbon liquids or other working fluids/chemicals having a dipole moment and exhibiting dielectric relaxation over change in an environmental variable such as temperature or applied frequency of electrical excitation.

Other aspects of the invention are also disclosed. For example, stated generally, the invention relates to a method for analyzing a working fluid to determine an attribute of the working fluid, by generating a dielectric relaxation spectrum of the permittivity of the working fluid. The dielectric spectrum is produced by varying an enviornmental variable affecting the permittivity of the working fluid (which may be temperature, or frequency) over a range including a special point at which the rate of change of the permittivity with the environmental variable is at a maximum. Then, the special point in the dielectric relaxation spectrum is identified from variation in the permittivity of the working fluid, and then features of the dielectric relaxation spectrum at the special point to a measure of the attribute of the working fluid.

In the specific embodiment disclosed below, the dielectric spectrum is generated by varying the temperature of the working fluid rather than the frequency of the applied electrical stimulation, for the reason that variation of either temperature or frequency will generate a dielectric spectrum, but the applied frequency can more easily be controlled to a constant value while varying temperature, than vice versa.

Additional aspects of the invention feature apparatus for performing the above analysis method. This apparatus may be in the form of a desk-top oil analyzer for use in an on-site application, or an integrated analysis device suitable for mounting directly to the mechanical system, e.g., in the form of an adapter insertable between the oil filter and oil filter mounting.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
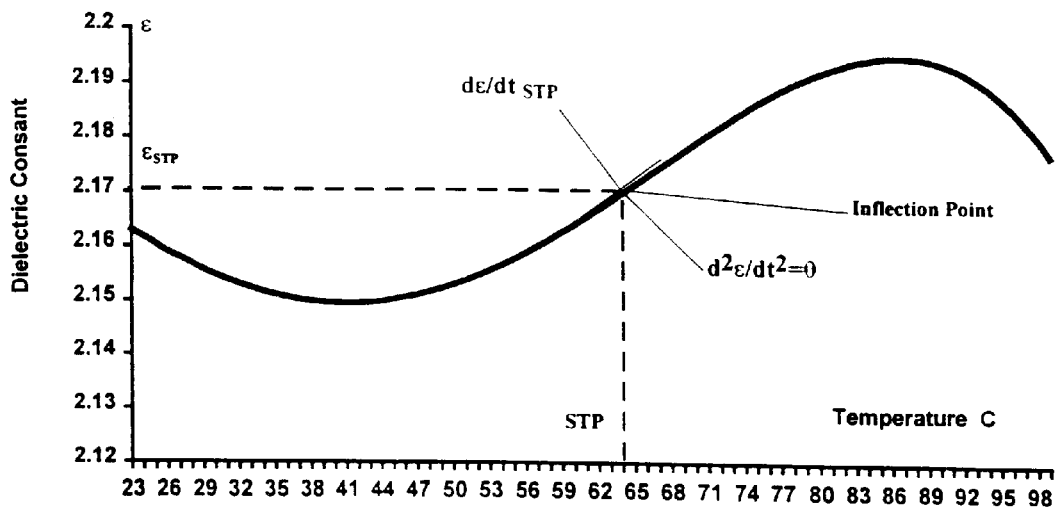
FIG. 1 is a plot illustrating the variation of the relative permittivity of oil as a function of temperature at a constant frequency, showing the inflection point which appears at the special temperature STP.

Before detailing implementations of the dielectric spectroscopy methods used in accordance with the present invention for measuring parameters of oil, a brief theoretical background for these methods will be provided.

Nearly all pure hydrocarbon liquids used as working fluids, when at near room temperature and atmospheric pressure, are dielectric, i.e., they do not conduct electric current, but have a permittivity $\epsilon$. (For the purposes of this patent application, permittivity $\epsilon$ will be expressed in relative units, i.e., relative to the permittivity $\epsilon_{ABS}$ of free space.) The value of the permittivity $\epsilon$ is a function of the tendency of the working fluid's molecules or molecular groups to become polarized (displaced) in such a way as to oppose externally applied electric fields E.

The displacement of molecules and molecular groups which leads to the dielectric effect, does not occur instantaneously upon application of an external electric field. Rather, there is a characteristic time for molecules or molecular groups to displace to their polarized or unpolarized positions. Accordingly, when an alternating electric field is externally applied to a dielectric working fluid, the permittivity of the working fluid will vary as a function of the frequency of the applied electric field, and generally will be larger for lower-frequency electric fields.

There are three mechanisms for polarization in working fluids which collaborate to produce the permittivity of the fluid at any given driving frequency. These mechanisms are electronic, atomic, and dipole (orientational) polarization.

Electronic and atomic polarization act at an atomic level, and are dominant at applied electric field frequencies above approximately $10^{12}$ Hertz; application of an electric field causes displacement of the electron cloud relative to the nucleus in each atom, in a manner to oppose the applied field, and furthermore, atomic nuclei move relative to one another.

Dipole polarization acts at a molecular level, and is dominant at relatively low frequencies. Dipole polarization results from rotation or re-orientation of molecules which have a dipole moment in a direction opposing the applied electric field. This mechanism requires molecular re-orientation of the working fluid, which requires a relatively long relaxation time to occur, which means that at higher frequencies dipole polarization disappears as an important contributor to the polarization phenomenon.

Accordingly, the permittivity of a working fluid at a relatively low applied frequencies is essentially constant over frequency, and primarily a result of dipole polarization mechanisms. As the applied frequency is increased, the permittivity of the fluid typically declines as the dipole polarization mechanism reduces in importance. At high (near optical) frequencies, the permittivity again has an essentially constant value, primarily as a result of electronic and atomic polarization.

It will be noted that materials with non-polar molecules do not exhibit dipole polarization. Most "light" petroleum products are non-polar, i.e., gasoline, diesel fuel, Vaseline oil. The permittivity $\epsilon$ for these liquids is typically in the range of 2.0–2.3, and does not vary substantially with frequency. In polar liquids, which include most multi-molecular chemical products such as spirits, carbon acids, acetone etc., the permittivity $\epsilon$ changes from a low frequency value to high frequency value, typically greater than about 2.3. "Heavy" petroleum products such as crude oil, lubricating oil, hydraulic fluid and heavy motor fuel are low concentration solutions of polar liquids and non-polar liquids, and accordingly have a permittivity $\epsilon$ which varies with frequency and is typically in the range of 2.1–2.5.

According to Debye's theorem, the permittivity for spherical molecules present in liquid can be written as:

$$\epsilon = \epsilon_\infty + \frac{\epsilon_0 - \epsilon_\infty}{1 + \omega^2 \tau^2} \qquad (1)$$

where $\epsilon$ is the real part of the complex permittivity, $\epsilon_\infty$ is the equilibrium permittivity at infinitely high frequency applied field, $\epsilon_0$ is the equilibrium permittivity with a steady applied field, $\omega$ is the cyclic frequency of the applied electric field, and $\tau$ is the characteristic dielectric relaxation time of the liquid.

Debye's definition of $\tau$ uses a molecular model of spheres moving in a viscous liquid. According to this definition, $\tau = 4\pi r^3 \eta / KT$, where r is the characteristic molecular radius, $\eta$ is the viscosity of the liquid, and T is the Kelvin temperature. From this definition of $\tau$, it can be seen that by varying the temperature T of the liquid varies its characteristic dielectric relaxation time $\tau$, with a similar effect on the permittivity of the liquid as a corresponding variation in the stimulating frequency $\omega$.

In accordance with the present invention, the permittivity of oil is measured as the liquid is stimulated at 6 MHz, i.e., $\omega = 2\pi(6 \times 10^6)$, which is equal to $1/\tau$ at a temperature of approximately 64 degrees Celsius. Varying the temperature T of the liquid over a range from 23 to 100 degrees Celsius, generates a curve of permittivity versus temperature such as shown in FIG. 1. Curves of this kind will be referred to as a "dielectric spectrum", or "spectrum of dielectric relaxation", because the curve demonstrates the effect of dielectric relaxation, which causes the permittivity to transition from its low frequency value of $\epsilon_0$ to its high frequency value of $\epsilon_\infty$. Notably, when the temperature T of the liquid is such that $\omega \tau = 1$ (which in the illustrated curve is at T=64° Celsius), there is an inflection point in the curve, at which the rate of change of the permittivity with temperature reaches its maximum value. This temperature at which $\omega\tau=1$ has special significance in determining parameters of the oil and will be referred to herein as the "Special Temperature Point" or STP. Viscosity, moisture and acid content measurements in accordance with the present invention are made by first locating the STP, and then determining values for T, $\epsilon$ and $\partial\epsilon/\partial T$, which are related to viscosity, moisture and acid content, as demonstrated below.

Other hydrocarbon liquids having a dipole moment, such as hydraulic fluid, will exhibit a similar dielectric spectrum with variation in temperature or applied frequency, albeit typically at different temperature and frequency ranges. Temperature variation alters the value of $\tau$, whereas frequency variation varies the value of $\omega$; variation of either produces a curve similar to that of FIG. 1 with a special point where $\omega=\tau$. Other chemicals having a dipole moment will also produce such a spectrum with variation in temperature, frequency, or potentially other environmental parameters which affect the value of $\tau$.

Figure 2:
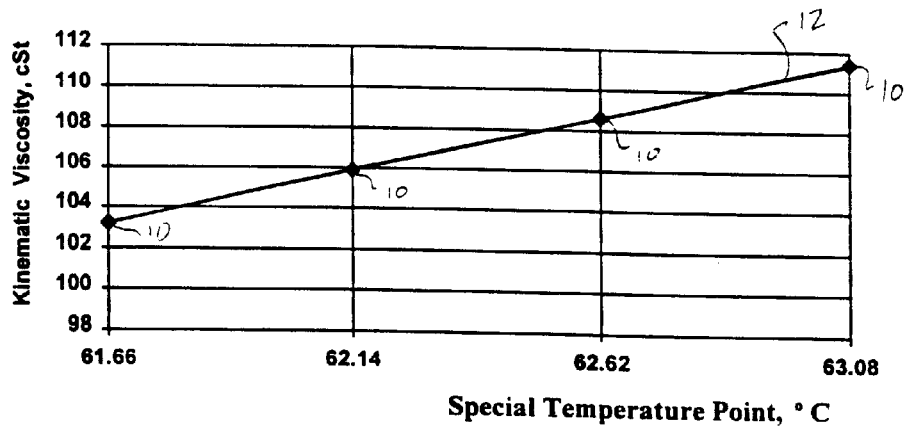
FIG. 2 is a plot illustrating the relationship between oil viscosity and the special temperature.

As can be seen from Debye's definition $\tau=4\pi r^3\eta/KT$, there is a linear dependence between $\tau$ and $\eta/T$. This dependence can be used to detect the fluid viscosity. Specifically, at the temperature $T_{STP}$ of the STP, Debye's definition can be written $\omega\tau=1=4\pi r^3\omega\eta T/KT_{STP}$. Collecting the temperature of the special temperature point $T_{STP}$ and all constant terms on the right side, this becomes $\eta=T_{STP}(K/4\pi r^3\omega)$. Thus, the viscosity $\eta$ of the fluid is linearly related by a number of constant terms, to $T_{STP}$, the temperature at the STP. FIG. 2 illustrates four data points 10 collected for four samples of a particular lubricating oil each having a different viscosity. The linear nature of the relationship between $\eta$ and $T_{STP}$ is apparent from FIG. 2, as shown by the best-fit straight line 12 shown on FIG. 2. From a plot of this kind, the measured temperature for the STP for a particular working fluid can be converted into a value for the viscosity $\eta$ by linear interpolation, i.e., by finding the point on the best fit line 12 in the plot of FIG. 2 corresponding to the temperature of the STP of a sample, and then determining the value of $\eta$ corresponding to that point.

Debye and Onsager have shown that the polarity of a pure dielectric liquid is determined by the quantity of polar molecules in the liquid, and the dipole moment $\mu$ of those molecules. At a fixed temperature, Debye and Onsager showed specifically a correlation between the permittivity decrement $\Delta\epsilon=\epsilon_0-\epsilon_\infty$ and the concentration of polar molecules:

$$\Delta\epsilon = \epsilon_0 - \epsilon_\infty = \frac{(\epsilon_0+2)(\epsilon_\infty+2)}{3} \frac{N\mu^2}{9\epsilon_{ABS}KT} \quad (2)$$

where N is the number of polar molecules per cubic centimeter, $\mu$ is the permanent dipole moment of those polar molecules, $\epsilon_{ABS}$ is the permittivity of free space and T is the absolute temperature.

Considering equation (2) in connection with working fluids such as lubricating oil and hydraulic fluid, it has been noted that oxidized hydrocarbon molecules exhibit a substantially greater polarization than unoxidized hydrocarbons. Accordingly, the concentration N of polar molecules in working fluid is roughly proportional to the concentration of oxidized molecules and thus to the acid content of the working fluid.

Figure 3A:
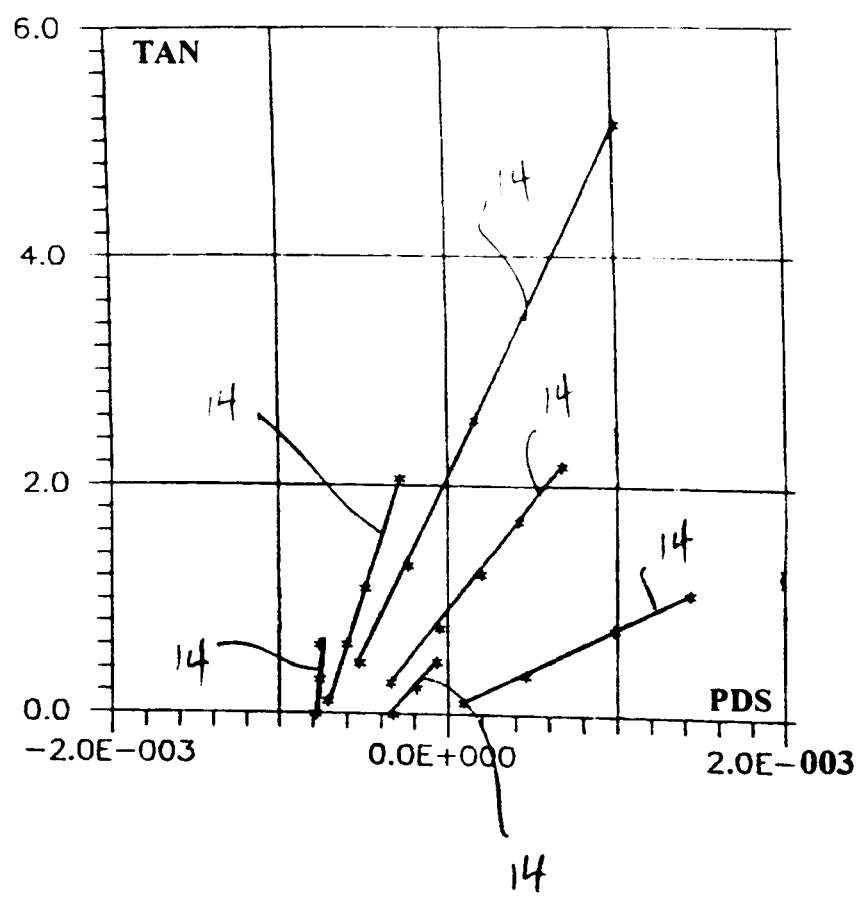
FIGS. 3A and 3B are plots illustrating the relationship between oil total acid number and the rate of change of permittivity with respect to temperature at the special temperature point, for a variety of working fluids.

Empirical analysis indicates that the quantity $\Delta\epsilon$ is proportional to the rate of change of permittivity $\epsilon$ with respect to temperature T at the STP, i.e., $\partial\epsilon/\partial T|_{STP}$. The value of $\partial\epsilon/\partial T$ at the STP is known as the Parameter of Dielectric Spectrum or PDS. Since $\Delta\epsilon$ is proporational to $\partial\epsilon/\partial T|_{STP}$, as a result of equation (2), the concentration of polar molecules, i.e. oxidized hydrocarbons, in working fluid, which is a measure of acid content, must also be proportional to PDS. This is seen in FIG. 3A, which shows variation in total acid number TAN as compared to PDS, for several grades of working fluids. Best-fit lines for the measured points for each grade of working fluid are shown. Note that each grade of working fluid shows a nearly linear relationship between variation in PDS and TAN, and that the best fit lines appear to lead from a common origin approximately at the point PDS=$-8.7\times10^{-4}$, TAN=$-0.6$. Thus a plot of PDS versus TAN for any grade of working fluid can be generated by measuring PDS and TAN and forming a straight line through the measured point and the point where PDS=$-8.7\times10^{-4}$, TAN=$-0.6$. This substantially simplifies the process of forming the appropriate plot for a given grade of working fluid.

Figure 3B:
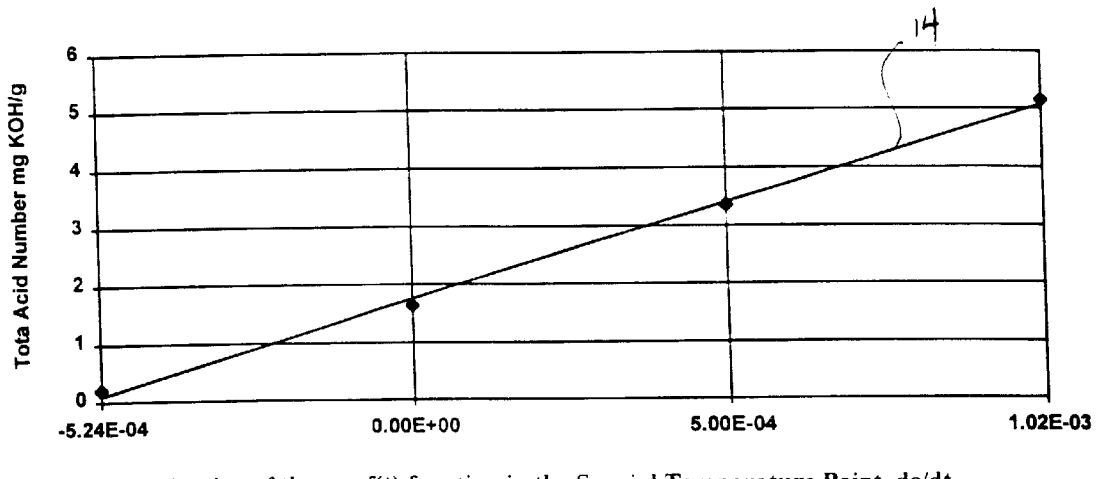

One plot of PDS versus TAN for a particular grade of working fluid is shown in FIG. 3B. From a plot of this kind, a measured PDS for a sample of this particular grade of working fluid can be converted into a value for TAN by linear interpolation, i.e., by finding a point on the best-fit line 14 of FIG. 3B corresponding to the measured PDS, and then determining the value of TAN corresponding to that point.

A primary source of contamination of working fluids in a mechanical system is by collection of water. A liquid petroleum product contaminated by water is described as consisting of two phases, a discontinuous phase (contamination) and a continuous phase (liquid).

The relationship between the electrical properties of heterogenous dielectrics and their respective phases has been the subject of several investigations. Wagner published his treatment for the case of spheres immersed in a medium of different permittivity, which according to the present invention is used as a model for water contamination in a working fluid. According to Wagner's theory, the dispersed phase in an external electric driving field can lead to surface polarization phenomena on the surfaces of the immersed spheres, the result of displacement of electrons relative to ions at the surfaces of the immersed spheres. As a result, each sphere becomes, in effect, a large dipole. Wagner identifies the dielectric relaxation parameters of the mixture as:

$$\epsilon_m = \epsilon_h + \frac{\epsilon_l - \epsilon_h}{1 + \omega^2 \tau_m^2} \quad (3)$$

$$\epsilon_l = \epsilon_c(1 + 3V)$$

$$\epsilon_h = \epsilon_c\left[1 - 3V\left(\frac{\epsilon_c - \epsilon_d}{2\epsilon_c + \epsilon_d}\right)\right]$$

$$\tau_m = \left[\frac{2\epsilon_c + \epsilon_d}{X_d}\right]\epsilon_{abs}$$

where $\tau_m$ is the relaxation time of the dispersion mixture, $\epsilon_m$ is the permittivity of the dispersion mixture, $\epsilon_{abs}$ is the permittivity of free space i.e. $8.854\times10^{-12}$ F/M, $X_d$ is the conductivity of the discontinuous phase, $\epsilon_d$ is the permittivity of the discontinuous phase, $\epsilon_c$ is the permittivity of the continuous phase, and V is the volume ratio of the discontinuous phase.

Thus, it can be seen that the permittivity of a fluid mixture will exhibit a dielectric relaxation spectrum, progressing from a low-frequency value of $\epsilon_l$ to a high frequency value of $\epsilon_h$, with an inflection point at a frequency $\omega=\tau_m$. This is in addition to the spectrum due to dielectric relaxation in the continuous phase, which occurs at the STP as described above.

Figure 4:
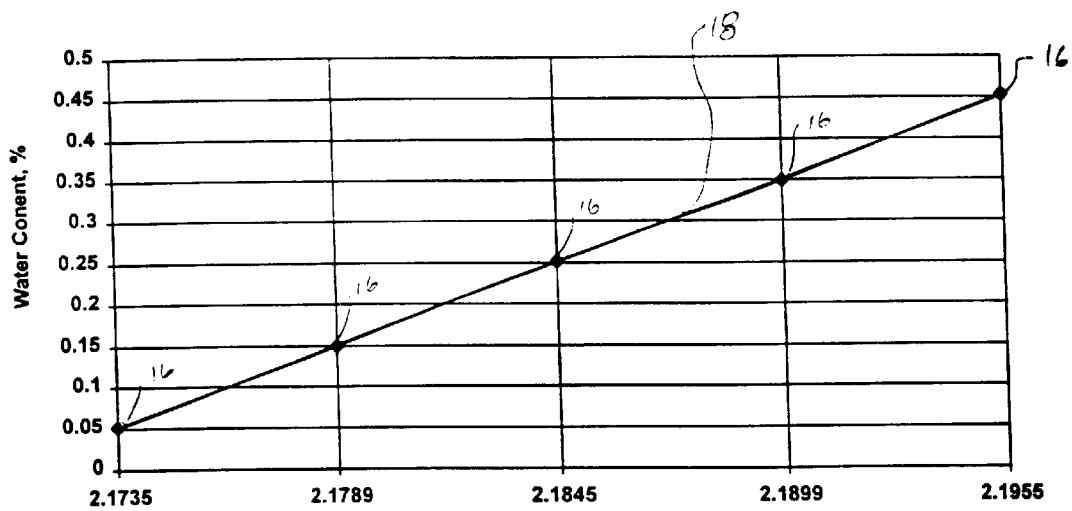
FIG. 4 is a plot illustrating the relationship between water content and the permittivity at the special temperature point.

Evaluating the expressions provided above, e.g., for water dispersed in oil, assuming $\epsilon_c=2.3$, $\epsilon_d=80$, $X_d=0.1$ Ω/m, it can be seen that at approximately room temperature, the spectrum of dielectric relaxation spectrum due to the immersed water spheres, appears at a frequency of approximately 130 MWz, substantially above the frequency of the spectrum due to dielectric relaxation in the continuous oil phase, which as noted above occurs at room temperature at approximately 6 MHz. Furthermore, considering this expression for $\epsilon_m$, it can be seen that, for a working fluid contaminated by water, at frequencies well below $\omega=1/\tau_m$, the permittivity is dominated by the expression for $\epsilon_1$ and is roughly proportional to the volume ratio V of contaminating water in the working fluid. This is borne out in FIG. 4, which illustrates the variation in the permittivity $\epsilon_{STP}$ at the STP of various samples of a particular grade of working fluid, at various levels of water content. Five points 16 have been plotted at positions corresponding to the measured water content and STP permittivity $\epsilon_{STP}$ of each sample. As can be seen from the best-fit line 18, these points are nearly collinear. Thus, from a plot of this kind, a measured STP permittivity $\epsilon_{STP}$ for a sample of this particular grade of working fluid can be converted into a value for water content by linear interpolation, i.e., by finding a point on the best-fit line 18 of FIG. 4 corresponding to the measured $\epsilon_{STP}$, and then determining the value of water content corresponding to that point.

With respect to density measurements, the Klausius-Mosotti equation for the permittivity $\epsilon_\infty$ is of use. The Klausius-Mosotti equation is:

$$\frac{\epsilon_\infty - 1}{\epsilon_\infty + 2} \frac{M}{\rho} = \frac{4\pi N r^3}{3} \quad (4)$$

where M is the molecular weight of the liquid, $\rho$ is the liquid density, N is Avogadro's ratio and r is the characteristic molecular radius. In accordance with the present invention, it is theorized that the molecular density $(M/r^3)$ has a constant value. Based on this assumption, equation (4) can be simplified to $\rho=c(\epsilon_\infty-1)/(\epsilon_\infty+2)$ where c is a constant. For most lubricating oils, the constant c has the approximate value c=3.118.

Returning momentarily to the above discussion of the dielectric relaxation spectrum of equation (1), shown in FIG. 1, note that at temperatures below the STP, $\tau \to \infty$ and therefore $\omega\tau \to \infty$. Thus, the permittivity at temperatures below the STP is essentially equal to $\epsilon_\infty$. (However, the simplified Klausius-Mosotti equation $\rho=c(\epsilon_\infty-1)/(\epsilon_\infty+2)$ shows that $\epsilon_\infty$ varies with density $\rho$. Density $\rho$ decreases with increasing temperature, as a result, below the STP, as temperature increases, $\epsilon_\infty$ and the measured permittivity decrease. This results in a negative slope in the permittivity spectrum at temperatures below the STP.)

Since the permittivity at temperatures below the STP are essentially equal to $\epsilon_\infty$, a permittivity measurement at a convenient temperature below the STP, e.g., at 15 degrees Celsius, can be readily converted to a measurement for density $\rho$ using the simplified Klausius-Mosotti equation $\rho=c(\epsilon_\infty-1)/(\epsilon_\infty+2)$. The value c=3.118 can be computed for a particular grade of oil, by measuring the density and permittivity of reference oil in the laboratory, and then solving the simplified Klausius-Mosotti equation for c. The resulting value of c can then be used in subsequent calculations converting a measured value of $\epsilon_\infty$ to a corresponding measure of the density $\rho$. Since $\epsilon_\infty$ is linearly related to temperature below the STP, measurements of $\epsilon_\infty$ at a number of temperatures below the STP can be fitted to a straight line function $\epsilon_\infty(T)$; then, $\epsilon_\infty$ can be found at a selected temperature below the STP, e.g., at 15 degrees Celsius, and then the computed $\epsilon_\infty$ at the selected temperature may be converted to the corresponding density $\rho$ at the selected temperature using the simplified Klausius-Mosotti equation $\rho=c(\epsilon_\infty-1)/(\epsilon_\infty+2)$ and the known value c=3.118.

With this theoretical background, an apparatus for analyzing parameters of a working fluid can be described.

Figure 5:
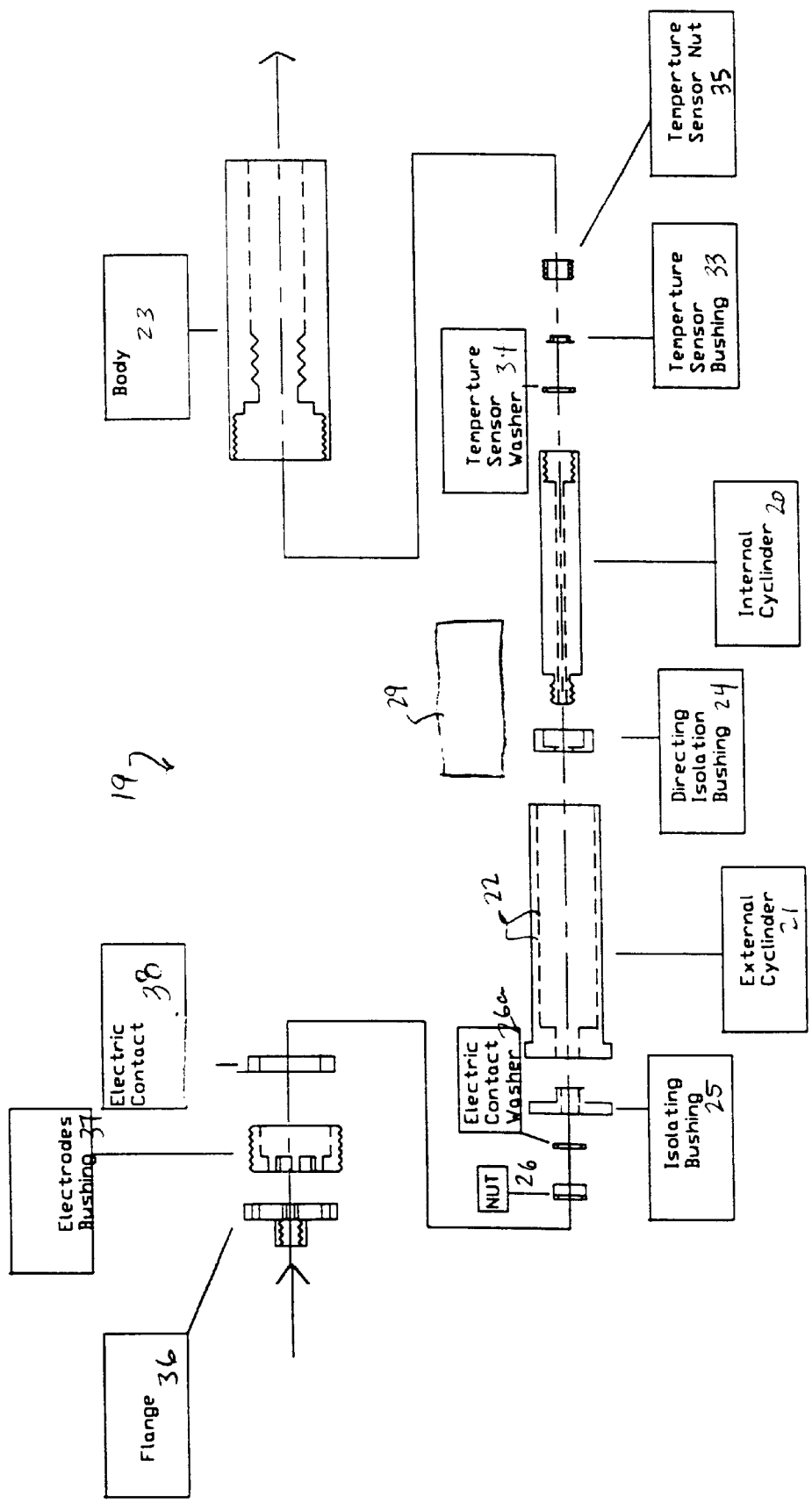
FIG. 5 is a disassembled, schematic diagram showing the components of a capacitive sensor useful in measuring permittivity of a working fluid in accordance with principles of the present invention.
Figure 6:
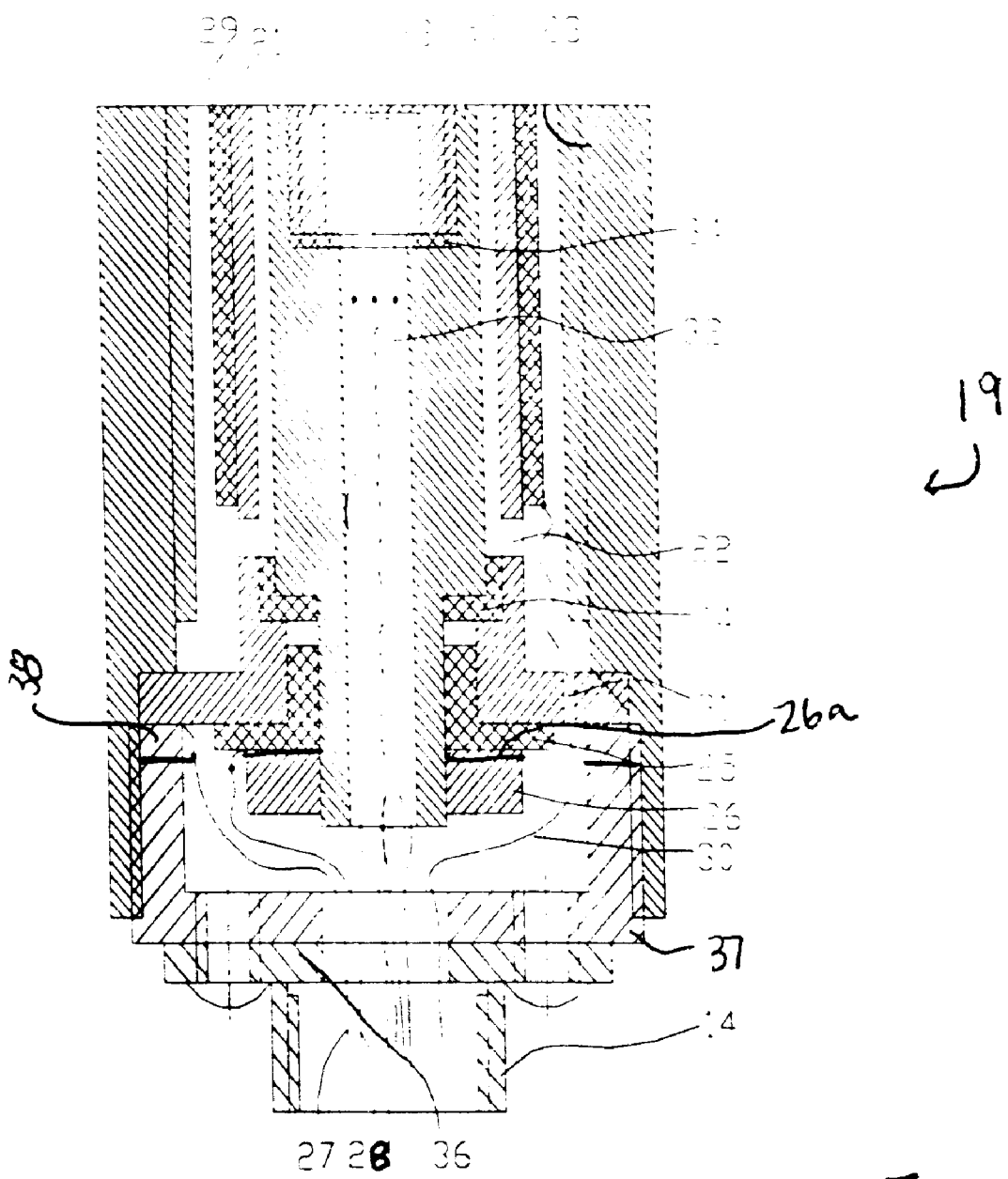
FIG. 6 is a cross-sectional diagram of the capacitive sensor of FIG. 5.

Referring now to FIGS. 5 and 6, a typical embodiment for a capacitive sensor 19 for working fluid analysis is shown. Sensor 19 comprises two coaxial and electrically isolated cylinders. A first cylinder 20 is positioned internally of the second cylinder 21. The cylinders serve as capacitive electrodes for working fluid which is between the cylinders. Radial holes 22 in the external cylinder 21 allow the working fluid to flow and freely circulate in a first annular gap (see FIG. 6) between the cylinder electrodes 20 and 21, thereby defining a permittivity sensing electric capacitor. A second annular gap is formed between outer cylinder electrode 21 and body 23 of the sensor. Working fluid flows into one of the first and second annular gaps and out the other annular gap to fill the sensor body with working fluid to be analyzed.

Electrode 20 is located within and electrically isolated from cylinder 21 by means of two dielectric bushings 24 and 25. A nut 26 is used to tighten cylinder electrode 21 onto cylinder electrode 20. An electrical contact washer 26a is captured between nut 26 and isolating bushing 25. The assembly of electrodes 20 and 21 are then assembled into body 23 and held in place by an electrodes bushing 37. A second electrical contact washer 38 is captured between outer electrode 21 and bushing 37.

Leads 28 and 27 are connected to cylinder electrodes 20 and 21 respectively, permitting external excitation of the electrical capacitor formed by cylinder electrodes 20 and 21. An end of lead 27 is captured between contact washer 38 and outer electrode 21 to ensure sound electrical contact. An end of lead 28 is captured between nut 26 and electric contact washer 26a to ensure sound electrical contact. Leads 27 and 28 may terminate in a sensor connector 14 (FIG. 8) which is part of a flange 36 external to electrodes bushing 37. The leads make electrical contact with sensor circuitry when the sensor unit 19 is plugged into a mating connector. Alternatively, in an in-line embodiment, leads 27 and 28 may be soldered directly to a printed circuit board positioned in flang 36, to minimize stray capacitance.

Cylinder electrode 20 has a bore for locating a temperature sensitive element 33 (FIG. 6) therein. The bore receives a washer 34 for supporting the temperature sensitive element 33 in a position spaced from the end of the bore. The bore is threaded to receive a press bushing 35 which holds the temperature sensitive element 33 in place. Press bushing and washer 34 hermetically seal the bore with the temperature sensor 33 inside, isolated from the working fluid. Electric leads 36 (FIG. 6) from the temperature sensor pass through washer 34 and channel 32 to the sensor connector 14, where these leads are connected to a mating connector.

An electrical resistance flexible heating element 29 is positioned surrounding external cylinder 21. Leads 30 connected to heating element 29 pass through an aperture 31 formed in external cylinder 21, and to the sensor connector 14 or printed circuit board.

Figure 7:
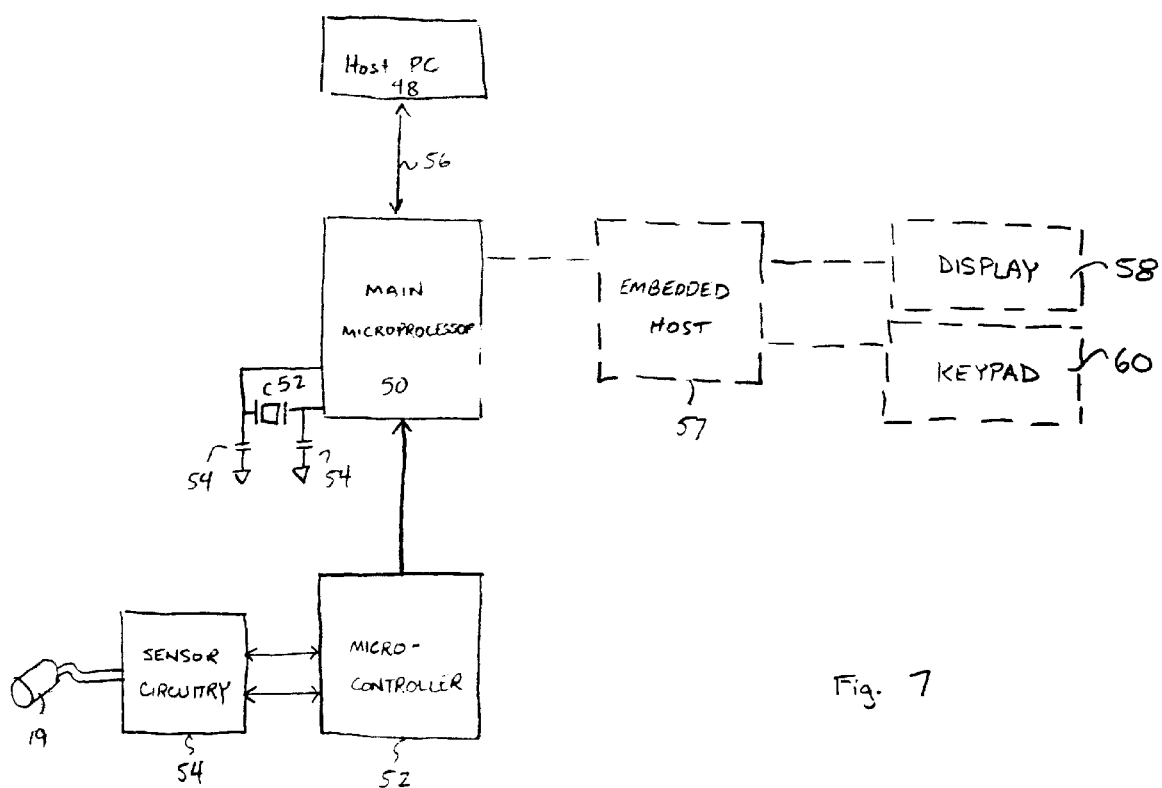
FIG. 7 is a block diagram of an electronic circuit for determining parameters of oil using the sensor of FIGS. 5 and 6.

Referring now to FIG. 7, a typical circuit for analyzing working fluid in accordance with the present invention includes a microprocessor, operating in response to a host such as a personal computer (PC) 48 using suitably prepared software, and controlling operations of the analyzer and performing mathematical calculations necessary to compute parameters of the working fluid. Microprocessor 50 utilizes a crystal clock circuit including a quartz crystal 52 and two loading capacitors 54, to derive an accurate timing clock. This clock is used to determine permittivity values of working fluid in the sensor, as described below.

In addition to microprocessor 50, the analyzing circuit includes a microcontroller 52. Microcontroller 52 may be an application specific integrated circuit or may be a programmed single-chip microcontroller such as are available from MICROCHIP Corporation of Chandler, Ariz. Microcontroller 52 is connected to sensor circuitry 54, which interfaces to capacitive sensor 19. As discussed below with reference to FIG. 8, the crystal clock oscillator circuitry of the microcontroller may be advantageously used as the active portion of an oscillator driving capacitive sensor 19 at the desired excitation frequency $\omega$. Other connections to the sensor 19 via sensor circuitry 54 control the electrical resistance heater 29, and read temperature readings from temperature sensor 35.

Microprocessor 50 generates one or several output signals indicative of the measured working fluid parameters. A serial or parallel external output connection may be made via signal lines 56 to an external host PC 48, which monitors the working fluid parameters determined by microprocessor 50 and generates suitable display. In an on-site desktop embodiment (shown in dotted lines), microprocessor 50 may be coupled by signal lines 56 to an embedded host 57 internal to the desktop unit, which is further connected to a display 58 for displaying working fluid parameter readings, and a keypad 60 which can be used by an operator to initiate working fluid analysis, program operative settings of the host 57 and display 58, or otherwise interact with the host and display under control of suitable software.

Figure 8:
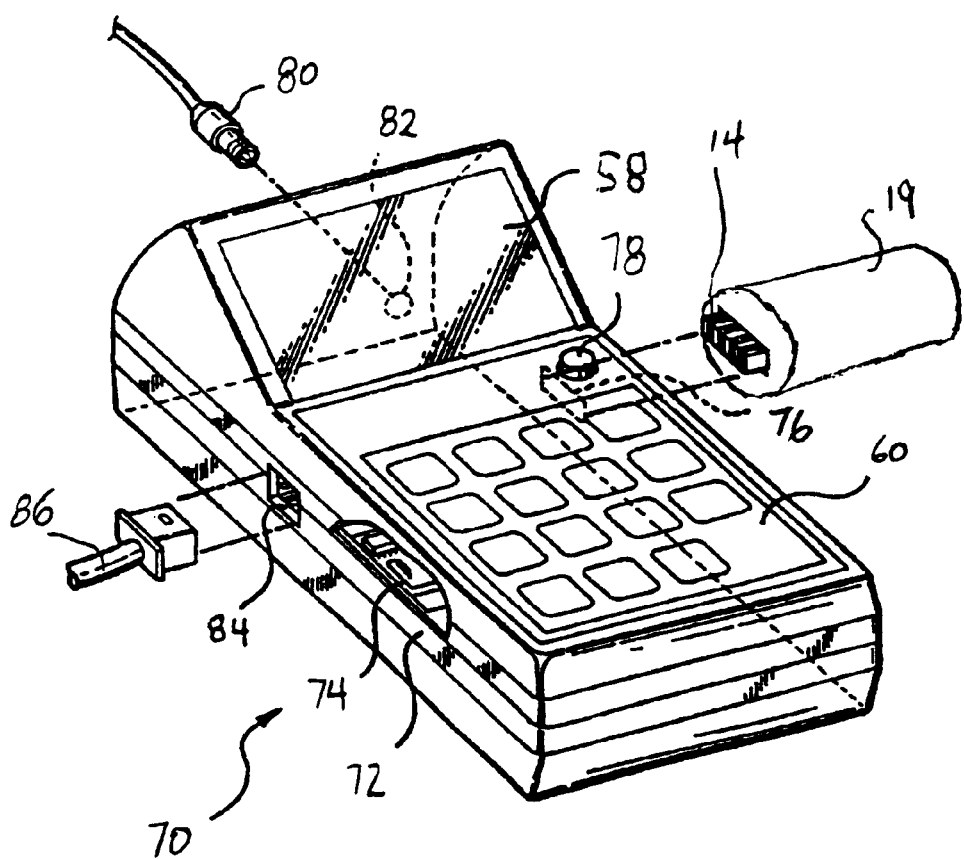
FIG. 8 is a perspective illustration of a desktop working fluid analyzer in accordance with principles of the present invention.

One example of such an on-site application is shown in FIG. 8.

In this embodiment, a desktop oil analyzer 70 includes a housing 72 which encloses a printed circuit board 74 carrying microprocessor 50, microcontroller 52 and sensor circuitry 54, embedded host 57, display 58 and keypad 60. One side of the housing 11 has a socket 76 into which the connector 14 of the capacitive sensor 19 may be inserted, so as to electrically connect the various electrical components of the capacitive sensor to the microcontroller. The socket 76 may be directly placed on the printed circuit board 74 so as to reduce the manufacturing complexity of the desktop analyzer 70.

The upper surface of the housing carries an ON/OFF switch 78 for applying operative power to the electrical components of the analyzer 70. Power may be provided by a battery mounted inside of housing 72 (of a high power type with 28 Volt output), or by an external DC power cord 80 inserted into a power jack 82 which may also be directly placed on the printed circuit board 74. Display 58 and keypad 60 are visible on the upper surface of the housing to permit an operator to interact with the microprocessor 50 to activate the analyzer in any desired manner.

Housing 72 further includes an opening for a serial connector jack 84, for connection to a serial cable 86 leading to a host computer (not shown). Jack 84 may also be directly placed on printed circuit board 74. Using such a connection, analyzer 70 may be externally controlled and/or parameter measurements made by analyzer 70 may be readily uploaded to a host computer for use in statistical analysis or historical record keeping.

Figure 9:
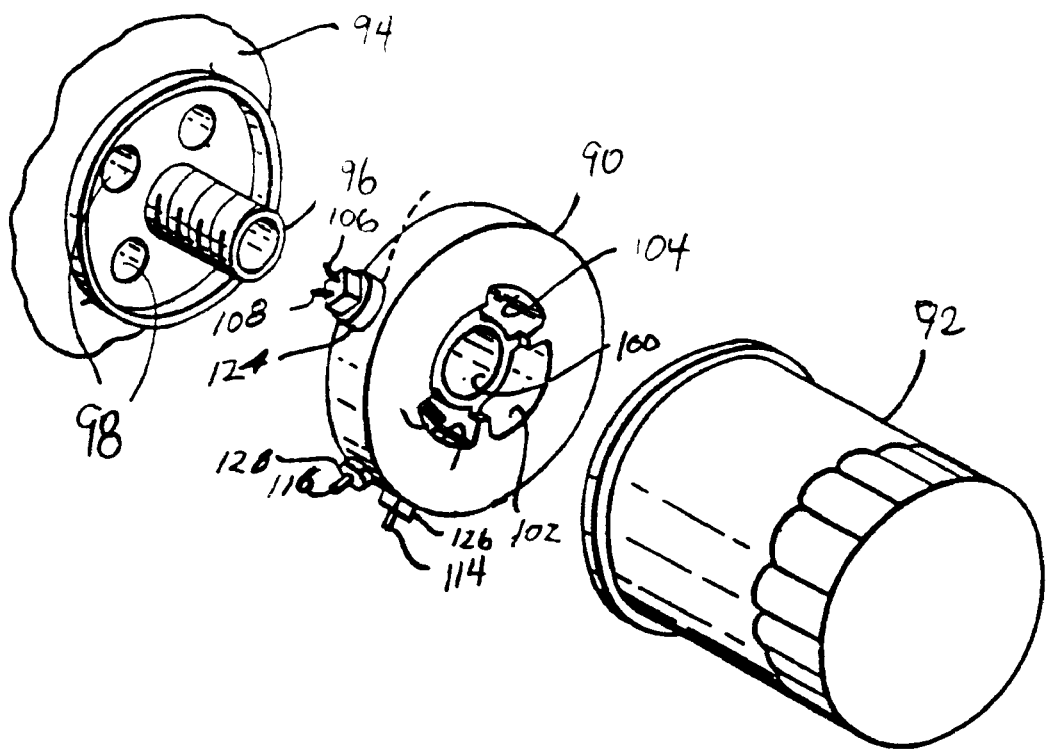
FIG. 9 is a perspective illustration of an on-line analyzer for insertion between a working fluid filter and working fluid filter connector in accordance with principles of the present invention.

Referring now to FIG. 9, in an alternative on-line embodiment of the present invention, microcontroller the circuitry of FIG. 7 and/or a portion thereof is incorporated into an adapter 90 which can be inserted between a working fluid filter 92 and a filter mount 94 in a mechanical system. Working fluid flowing through the filter from stem 96 to apertures 98 will pass through adapter 90. Stem 96 passes through an aperture 100 in adapter 90 to permit normal operation of the fluid filter 92. Adapter 90 may be suitably formed with cylindrical capacitive structures positioned within area 102 and 104 of adapter 90 for measuring the permittivity of oil passing out of filter 92. Adapter 90 houses a suitably shaped temperature sensor and electrical resistance heater, hermetically sealed from external environment and from the oil passing through filter 92. Electrical connections such as 106, 108, 114 and 116 are attached to leads from external control circuitry (not shown). Connections 106, 108, 114 and 116 are hermetically sealed and isolated from the body of adapter 90 by bushings 124, 126 and 128.

Figure 10:
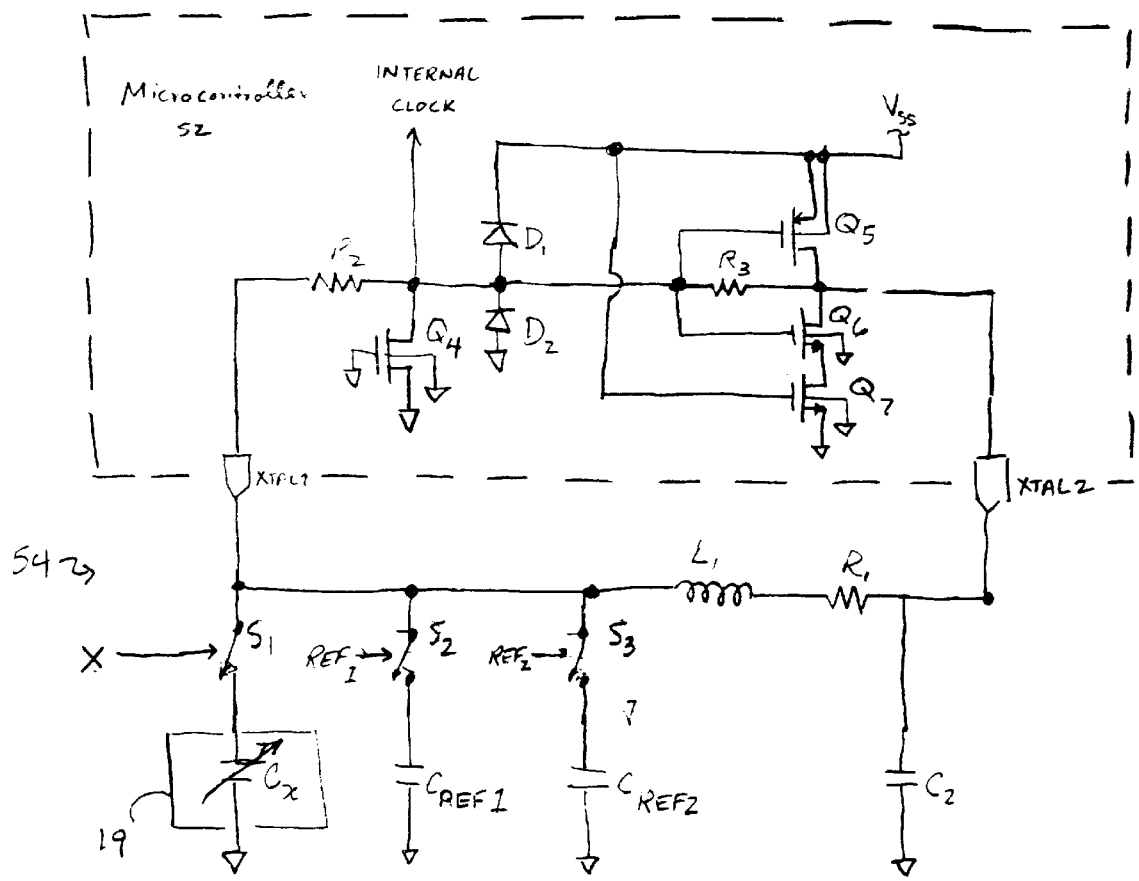
FIG. 10 is an equivalent circuit diagram of the oscillator circuitry used in the electronic circuit of FIG. 7.

FIG. 10 illustrates the circuitry in microcontroller 52 and sensor circuitry 54 responsible for stimulating sensor 19 with a constant frequency oscillating signal to permit measurement of the capacitance of the sensor 19, and thus the permittivity of the fluid in sensor 19. As noted above, this circuitry makes use of the crystal clock oscillator circuitry integrated into microcontroller 52, which utilizes two pins XTAL1 and XTAL2 of microcontroller 52. In an equivalent circuit diagram for this internal circuitry, pin XTAL2 is connected to the output of a CMOS inverter internal to microcontroller 52, consisting of a PMOS transistor $Q_5$ connected between the power supply of microcontroller 52 and pin XTAL2, and two NMOS transistors $Q_6$ and $Q_7$, which are series connected between pin XTAL2 and ground. The gate terminals of transistors $Q_5$ and $Q_6$ are all connected to a common input node, whereas the gate of transistor $Q_7$ is connected to the power supply of microcontroller 52. This inverter, produces an output signal on the XTAL2 pin which is a gain-enhanced version of an input signal applied to the gate terminals of transistors $Q_5$ and $Q_6$. Unlike most other circuitry in microcontroller 52, transistors $Q_5$ and $Q_6$ are operated in their linear region when the oscillator is in operation. The gate terminals of transistors $Q_5$ and $Q_6$ are connected via resistor $R_2$ to pin XTAL1. (Clamping diodes D1 and D2 and transistor $Q_4$ provide signal biasing and clamp protection.) Accordingly, a positive feedback is produced whenever an impedance is placed between terminals XTAL1 and XTAL2. The result will be oscillation at the frequency where the phase shift and loop gain produce positive feedback, which will be very nearly sinusoidal.

In a typical application, a quartz crystal is connected between the XTAL1 and XTAL2 pins, and fixed loading capacitors are connected between the XTAL1 and XTAL2 pins and ground, respectively. In this application, the frequency of oscillation is determined primarily by the size of the quartz crystal. In the present application, instead of connecting a quartz crystal between the XTAL1 and XTAL2 pins, an inductor $L_1$ is connected between these pins, and capacitors $C_2$, $C_{REF1}$, $C_{REF2}$ and $C_X$ are connected between the XTAL1 and XTAL2 pins and ground. The inductance of inductor $L_1$ and equivalent capacitance of the capacitors connected to the XTAL1 and XTAL2 pins, determines the oscillation frequency of the oscillator circuit of microcontroller 52. (Inductor $L_1$ has an inherent winding resistance, which is modeled in the equivalent circuit diagram of FIG. 10 by a series resistance $R_1$.)

The oscillating circuitry can be used as a precise capacitance measuring tool, by alternately connecting calibrating and unknown capacitances to pin XTAL1. As shown in FIG. 10, a fixed capacitance $C_2$ is coupled between pin XTAL2 and ground; however, three capacitors $C_{REF1}$, $C_{REF2}$ and $C_X$ are connected to pin XTAL1 via relay switches $S_1$, $S_2$ and $S_3$. Relays are used to minimize parasitic capacitances in the switches. $C_{REF1}$ and $C_{REF2}$ are fixed-value reference capacitances which form part of sensor circuitry 54. $C_X$ represents the equivalent capacitance between internal and external cylinders 20 and 21 of sensor 19, and is the capacitance that will vary as a function of the permittivity of the working fluid in sensor 19. The control windings of relay switches $S_1$, $S_2$ and $S_3$ are coupled to digital control signals X, REF1 and REF2 which are produced by microcontroller 52 in the manner described below, so as to selectively connect one or more of capacitors $C_{REF1}$, $C_{REF2}$ and $C_X$ between pin XTAL1 and ground.

In use of the above circuitry, a measurement is made of the capacitance of sensor 19. It will be appreciated that the capacitance between the inner and outer cylinders 20 and 21 of sensor 19 will be a function of the permittivity of the working fluid interposed between those cylinders. One method for measuring the permittivity from capacitance is described by Fredrich Ehme in *Dielectric Measurement*, published 1967 by Mir publishing, Moscow, Russia (Russian translation). According to this method, the permittivity $\epsilon_{liquid}$ of a dielectric filling the space between the plates of a capacitive structure, may be computed from $$\epsilon_{liquid} = \frac{C_{liquid} - C_{stray}}{C_{vacuum}} \quad (5)$$

In this equation, $C_{liquid}$ represents the measured capacitance of the structure when the dielectric is imposed between the plates, $C_{vacuum}$ represents the capacitance of the capacitive structure, excluding stray capacitance, when vacuum is imposed between the plates, and $C_{stray}$ is the stray capacitance associated with the capacitive structure that is not affected by the dielectric between the plates.

It should be noted that $C_{vacuum}$ and $C_{stray}$ are unknown values for any particular capacitive structure, and must be empirically computed. Furthermore, $C_{vacuum}$ and $C_{stray}$ likely will vary with temperature due to thermal expansion and other temperature-related effects on the capacitive structure.

To compute values for $C_{vacuum}$ and $C_{stray}$ at a given temperature, the capacitance of the capacitive structure is measured with two different dielectric liquids of known permittivity imposed between the plates. Then, the two measured capacitance values, and known permittivity values for the two dielectric liquids used in the measurements, are substituted for $C_{liquid}$ and $\epsilon_{liquid}$ in equation (5), forming two simultaneous equations with two unknowns $C_{vacuum}$ and $C_{stray}$. These simultaneous equations can then be solved for $C_{vacuum}$ and $C_{stray}$ to find values for these two capacitances at the given temperature. This process can be repeated for a number of temperatures, e.g., 35 different temperature points spread across a temperature range of interest (e.g., 20–100 degrees Celsius), to collect a number of data points for $C_{vacuum}(T)$ and $C_{stray}(T)$. These data points are then fitted to a third-order polynomial equation by a least-squares method to form third-order equations for $C_{vacuum}(T)$ and $C_{stray}(T)$. Subsequently, a measured value for $C_{liquid}$ at a given temperature can be converted to $\epsilon_{liquid}$ for the same temperature using equation (5) and values of $C_{vacuum}$ and $C_{stray}$ at that temperature generated from the third-order polynomial.

Figure 11:
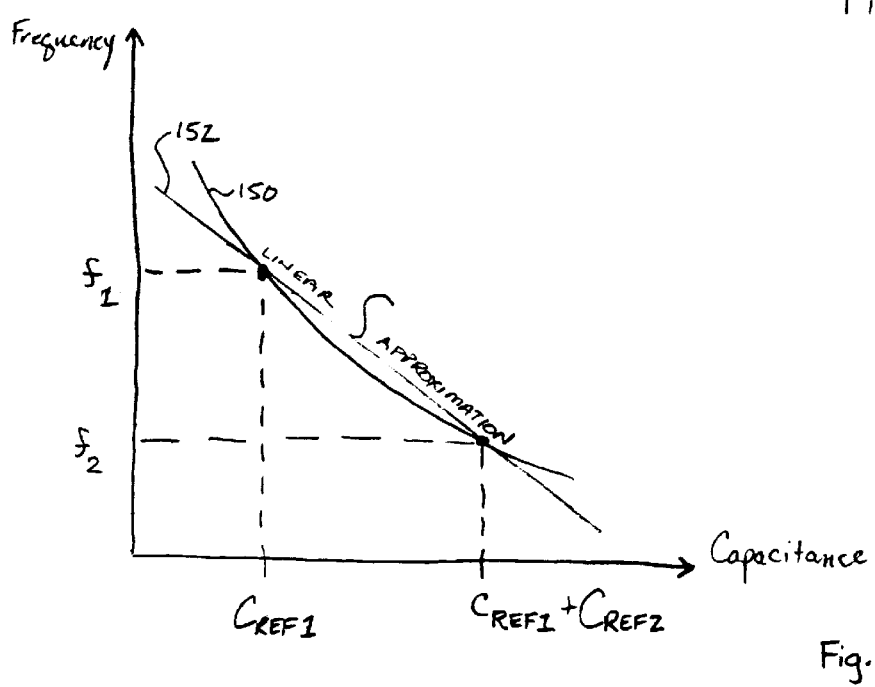
FIG. 11 is a plot of the relationship of capacitance and output frequency of the oscillator circuitry of FIG. 10.

FIG. 11 illustrates one methodology for measuring the equivalent capacitance $C_X$ of the sensor 19 and thus the permittivity of the working fluid in the sensor 19. In this method, the oscillator frequency produced by two known capacitances is measured, and then compared to the oscillator frequency produced by the unknown capacitance $C_X$. Specifically, as a first step, switches $S_1$ and $S_3$ are turned "off" while switch $S_2$ is turned "on", so as to connect only capacitor $C_{REF1}$ to pin XTAL1 of microcontroller 52. In this configuration, the oscillator circuitry will produce an oscillation frequency which is a function of the inductance $L_1$ and the capacitances $C_{REF1}$ and $C_2$. This frequency is shown in FIG. 11 as the frequency $f_1$. After this frequency has been measured, then switch $S_3$ is turned "on" while switch $S_1$ is maintained "off" and switch $S_2$ is maintained "on". In this configuration, the oscillator circuitry will produce an oscillation frequency which is a function of the inductance $L_1$ and the capacitances $C_{REF1}$, $C_{REF2}$ and $C_2$. This second frequency is shown in FIG. 11 as the frequency $f_2$.

As can be seen from curve 150 in FIG. 11, variation in the capacitance value applied to the XTAL1 pin of microcontroller 52, produces a corresponding nonlinear variation in the oscillator frequency. However, over small ranges of capacitance variation, a linear approximation can be made to the curve 150, as shown by line 152 in FIG. 11. A linear approximation such as line 152 can be established my measuring two points on curve 150 and then mathematically computing a line passing through those points, as has been done to produce line 152 from the points ($C_{REF1}$, $f_1$) and ($C_{REF1}+C_{REF2}$, $f_2$).

Using this linear approximation, an unknown capacitance value can be measured. Specifically, to measure the value of the capacitance $C_X$ produced by sensor 19, switch $S_1$ is turned "on" and switches $S_2$ and $S_3$ are turned "off", to thus connect only capacitance $C_X$ to the XTAL1 pin of microcontroller 52. In this configuration, the frequency of the oscillator in microcontroller 52 is measured, which will be known as $f_X$. Using the linear approximation described above, the value of $C_X$ can be derived from $f_X$ from the equation $$C_X = C_{REF1} + C_{REF2} \frac{f_x - f_2}{f_1 - f_2} \quad (6)$$

The resulting computed value for $C_X$, which is proportional to the permittivity of the working fluid in sensor 19, can then be used as described above to produce values for the viscosity, water content, acid content and density of the working fluid.

To maximize measurement accuracy, capacitor $C_{REF1}$ is chosen to have a capacitive value at the lower end of the range of capacitive values produced by sensor 19. Further, capacitor $C_{REF2}$ is chosen to have a capacitive value approximately equal to about one-half of the span of variation in the capacitive values produced by sensor 19. Doing so ensures that the linear approximation line 152 shown in FIG. 11 is as close as possible to the actual curve 150 over the range of measurements that will be made. In one embodiment, $C_{REF1}$ has a value of 25 picofarads and $C_{REF2}$ has a value of 2 picofarads, to facilitate measuring a capacitive range of about 24–28 picofarads produced under various conditions by sensor 19. Furthermore, to ensure that the special temperature point $T_{STP}$ is within a reasonable temperature range, the values for $L_1$, $R_1$. and $C_2$ should be selected so that the excitation frequency applied to the working fluid places the special temperature within this temperature range.

Figure 12A:
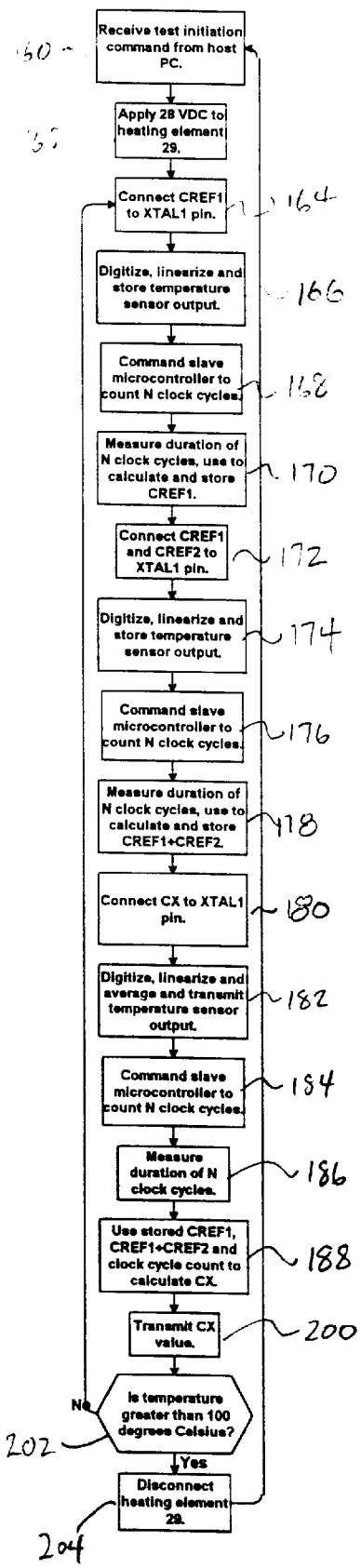
FIG. 12A is a flow chart of operations performed by the microcontroller of FIG. 7.

Referring now to FIG. 12A, an explanation will be made of the actions performed by microprocessor 50 in performing a capacitance measurement as part of oil analysis. This process begins in step 160 when microprocessor 50 receives a test initiation command from the host PC 48 or embedded host 57. In response, in step 162, microprocessor 50 applies 28 Volts DC to the heating element 29 to begin the process of heating the oil in the sensor over the temperature range.

Microprocessor 50 then enters a loop comprising steps 164–202, in which measurements of the capacitance $C_X$ are made. Each pass through this loop performs a measurement of the capacitance $C_X$, and records this capacitance as well as the temperature at the time of the measurement.

As noted above, the capacitance $C_X$ is measured with reference to the capacitance of two capacitors of known value, $C_{REF1}$ and $C_{REF1}$. Each pass through the loop of steps 164–202 performs a measurement of the oscillator frequency produced by connecting $C_{REF1}$ and $C_{REF1}$ to the XTAL1 pin of microcontroller 52, and then uses this information to compute the capacitance of $C_X$. This recalibrates the capacitance measurements each time through the loop of steps 164–202, reducing the effect of drift in the values of components in the sensor circuitry over time or temperature variation.

Accordingly, in step 164, microprocessor 50 initiates a measurement of $C_{REF1}$ by controlling switch $S_2$ (either directly or via a command to microcontroller 52) to connect $C_{REF1}$ to the XTAL1 pin of microcontroller 52. This causes the oscillator of microcontroller 52 to operate at a frequency related to the capacitance of $C_{REF1}$. Next, in step 166, microprocessor 50 reads and stores a temperature sensor reading from the temperature sensor, either directly or through microcontroller 52. Next in step 168, microprocessor 50 instructs microcontroller 52 to count N clock cycles. At the same time, microprocessor 50 begins counting clock cycles of the clock in microprocessor 50. In response to the command delivered in step 168, microcontroller 52 counts N cycles of its clock (the frequency of which is determined by the capacitance $C_{REF1}$). After counting N clock cycles, microcontroller 52 delivers a confirmation to microprocessor 50. Upon receiving this confirmation, microprocessor 50 halts counting its own clock cycles, and in step 170, microprocessor 50 converts its clock cycle count to a measure of the duration of the N clock cycles counted by microcontroller 52, and thus the frequency of the oscillator in microcontroller 52. This is then used to calculate and store a value for $C_{REF1}$ which can later be used in connection with equation (6) to compute a value for $C_X$.

Next, in steps 172–178, microprocessor 50 computes a value for $C_{REF1}+C_{REF2}$ in a similar manner. Specifically, in step 172, microprocessor 50 controls switches $S_2$ and $S_3$ to connect $C_{REF1}$ and $C_{REF2}$ to the XTAL1 pin of microcontroller 52. Then in step 174, microprocessor 50 measures and stores the temperature sensor output. Next in step 176, microprocessor 50 commands microcontroller 52 to count N clock cycles and then return a confirmation. Finally in step 178, microprocessor 50 measures, using a clock cycle count made by microprocessor 50, the duration of the N clock cycles counted by microcontroller 52, and converts this to a value for $C_{REF1}+C_{REF2}$.

Next, in steps 180–188, microprocessor 50 computes a value for $C_X$ in a similar manner. Specifically, in step 180, microprocessor 50 controls switch S1 to connect $C_X$ to the XTAL1 pin of microcontroller 52. Then in step 182, microprocessor 50 measures the temperature sensor output. This temperature sensor measurement is then averaged with the temperature sensor measurements made in steps 166 and 174 to produce an average temperature sensor reading. This reading is then transmitted to the host PC 48 or embedded host 57. Next in step 184, microprocessor 50 commands microcontroller 52 to count N clock cycles and then return a confirmation. In step 186, microprocessor 50 measures, using a clock cycle count made by microprocessor 50, the duration of the N clock cycles counted by microcontroller 52. Finally, in step 188, the stored values for $C_{REF1}$, $C_{REF2}$ and the clock cycle count obtained in step 186 are converted to a measurement for $C_X$, using the linear approximation method illustrated in equation (6) and FIG. 11. In step 200, this value for $C_X$ is transmitted to the host PC 48 or embedded host 57.

After the preceding steps, a capacitance measurement has been made for one temperature point. This process should then be repeated for subsequent temperature points over the entire temperature range, which in the present example is from room temperature to 100 degrees Celsius. Accordingly, in step 202, microprocessor 50 determines whether the temperature sensor reading is greater than 100 degrees Celsius. If not, microprocessor 50 returns to step 164 to begin the process of taking another temperature and capacitance reading. If the temperature sensor reading is greater than 100 degrees Celsius, then microprocessor 50 proceeds to step 204, in which the heating element is disconnected, end the test. Microprocessor 50 then returns to step 160 to await another test initiation command from the host.

Figure 12B:
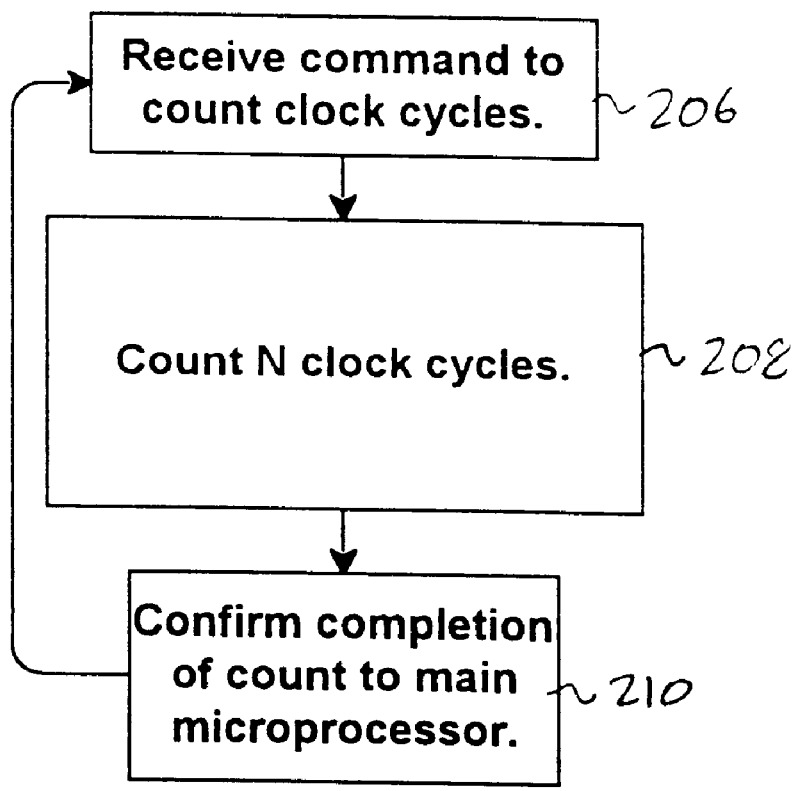
FIG. 12B is a flow chart of operations performed by the microprocessor of FIG. 7.

Referring now to FIG. 12B, the operations of the microcontroller 52 can be explained. Microcontroller 52 will wait in step 206 until it receives a command from microprocessor 50 to count clock cycles. Once this command is received, in step 208 microcontroller 52 will count N clock cycles, and then in step 210, microcontroller 52 will confirm to microprocessor 50 that it has completed its clock cycle count. Microcontroller 52 will then return to step 206 to await a subsequent command to count clock cycles.

Figure 12C:
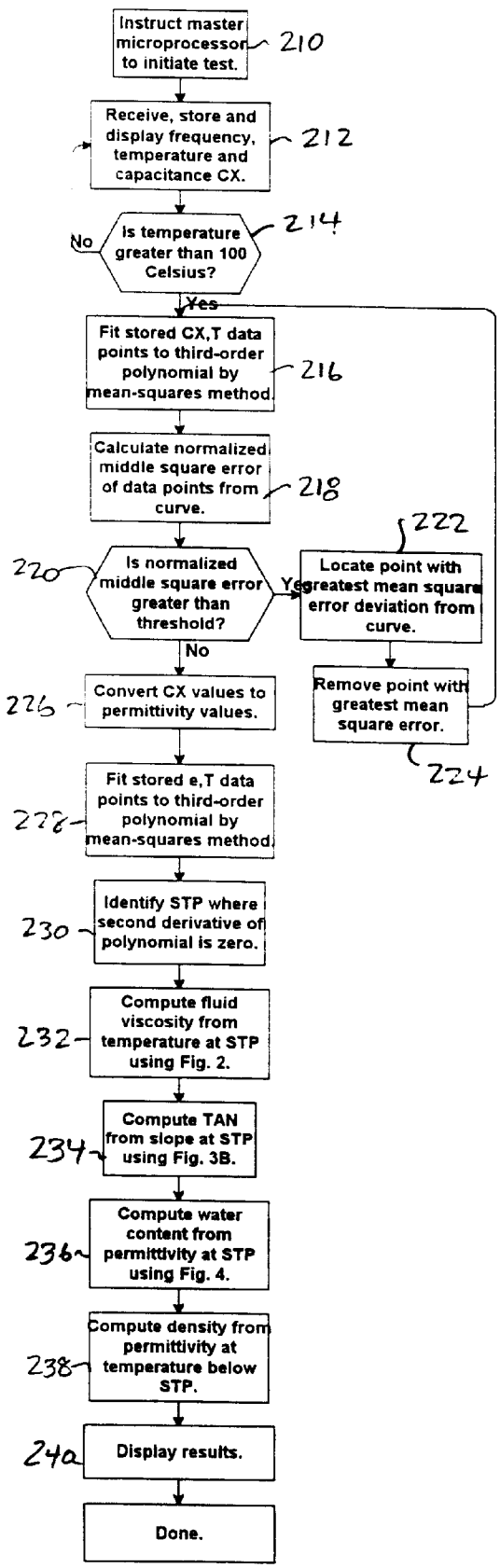
FIG. 12C is a flow chart of operations performed by a host PC interacting with the circuitry of FIG. 7.

Referring now to FIG. 12C, the operations of the host PC 48 or embedded host 57 in collecting and analyzing a dielectric spectrum can be explained. Initially, in step 210, the host instructs microprocessor 50 to initiate collection of data points for the dielectric spectrum. In response, the host receives a series of transmissions from microprocessor 50, each including a temperature measurement and a corresponding capacitance measurement for $C_X$. These values are received and stored in step 212. Then, in step 214, the host determines whether the spectrum has been completed, by determining in this case whether the last received temperature reading is greater than 100 degrees Celsius. If not, the host returns to step 212 to receive the next temperature and capacitance measurement.

After the entire spectrum has been collected, the host proceeds to step 216, in which the temperature and $C_X$ data points collected in step 212 are fitted to a third-order polynomial by a mean-squares curve fitting method. The details of mean-squares curve fitting are well known and this function is provided by many commercial software packages for spreadsheets and the like, and accordingly will not be elaborated here. After fitting the third-order polynomial, the host determines whether the data is reasonably well fitted to the curve. Specifically, in step 218 the host calculates the normalized middle square error of data points from the fitted curve, and then in step 220 the host compares the middle square error to a threshold. If the middle square error is greater than the threshold, then it is determined that there are erroneous data points included in the curve fit. In this case, the host proceeds to step 222, in which the host locates the point with the greatest mean square deviation from the curve. This point is likely to be erroneous. Accordingly, in step 224, this point is removed from the spectrum, and then the host returns to step 216 to re-fit the remaining points to the third-order polynomial.

When the middle square error is reduced below the threshold in step 220, the host proceeds to step 226 to begin oil parameter analysis. As a first step 226, the stored $C_X$ values are converted to permittivity values, by substituting $C_X$ into equation (5) using values for $C_{vacuum}(T)$ and $C_{stray}(T)$ for the temperature at which $C_X$ was measured. Next in step 228, the resulting $\epsilon$,T data points are fitted to a third-order polynomial by a mean-squares method, resulting in a third-order polynomial expression for permittivity $\epsilon$ as a function of temperature T.

In step 230 the host uses an expression, derived from the third-order polynomial, for the second derivative of the E,T curve, to find the point at which the second derivative of the curve is zero, which is the STP of the curve. In step 232, the temperature at the STP is converted into a measure of fluid viscosity using a plot of fluid viscosity versus temperature of STP such as FIG. 2. In step 234, the host derives an expression for the slope $d\epsilon/dT$ of the third-order polynomial, and then computes this slope at the STP and uses this slope, in connection with a plot such as FIG. 3, to determine a value for the TAN of the oil. In step 236, the value of the permittivity $\epsilon$ at the STP is used in connection with a plot such as FIG. 4, to compute the water content of the oil. Finally, in step 238, the value of the permittivity e at a temperature below the STP, e.g. at 15 degrees Celsius, is used in connection with the simplified Klausius-Mosotti equation $\rho=c(\epsilon_\infty-1)/(\epsilon_\infty+2)$ discussed above, to compute the density $\rho$ of the oil. These values are then displayed in step 240, and the oil analysis is done.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, temperature variation in the sample of oil being analyzed, may be produced by cooling rather than heating. In such an embodiment, a Peltier effect element or other cooling element would be used in place of a resistive heating element. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method for analyzing a working fluid to determine the viscosity of the working fluid, comprising the steps of
   measuring the permittivity of the working fluid while varying the temperature of the working fluid over a temperature range, the temperature range including a special temperature at which the rate of change of the permittivity over temperature is at a maximum,
   identifying the special temperature from variation in the permittivity of the working fluid over temperature,
   converting the value of the special temperature to a measure of viscosity of the working fluid.

2. The method of claim 1 wherein identifying the special temperature comprises
   fitting measurements of the permittivity of the working fluid at a plurality of temperatures to a mathematical model of an expected curve of the variation in the permittivity over temperature, and
   locating an inflection point in the mathematical model curve, and
   identifying the temperature of the inflection point as the special temperature.

3. The method of claim 1 wherein the working fluid is a lubricating oil.

4. The method of claim 1 wherein the working fluid is hydraulic fluid.

5. Apparatus for analyzing a working fluid of a mechanical system to determine the viscosity of the working fluid, comprising
   a housing,
   a permittivity measuring circuit including a capacitive sensor to be positioned in the working fluid,
   a heat transfer device associated with the sensor for varying the temperature of the working fluid over a temperature range,
   a temperature sensor for measuring the temperature of the working fluid,
   a storage device storing a plot relating viscosity to measured special temperature,
   a control circuit connected to the capacitive sensor, heat transfer device, and temperature sensor, the control circuit measuring viscosity of the working fluid by
      activating the heat transfer device to vary the temperature of the working fluid over a temperature range including a special temperature at which the rate of change of the permittivity over temperature is at a maximum,
      activating the permittivity measuring circuit and temperature sensor to measure the permittivity and temperature of the working fluid as temperature is varied over the range,
      identifying the special temperature from variation in the permittivity of the working fluid over temperature, and
      converting the value of the special temperature to a measure of viscosity of the working fluid, based on the stored plot.

6. The apparatus of claim 5 wherein the heat transfer device is an electrical resistance heater.

7. The apparatus of claim 5 further comprising
   a display mounted on said housing, and
   a keypad mounted on said housing, wherein
      said capacitive sensor extends from said housing to permit immersion of said sensor in a sample of working fluid to be analyzed, and
      wherein said control circuit is connected to said display and keypad to prompt a user via said display to analyze a sample of working fluid, and responsive to keystrokes upon said keypad to measure the viscosity of the sample of working fluid.

8. The apparatus of claim 5 wherein said housing is sized for mounting to the mechanical system, the capacitive sensor being positioned in the flow of working fluid in the mechanical system.

9. The apparatus of claim 8 wherein said housing is sized for mounting between a working fluid filter and the mechanical system.

10. The apparatus of claim 5 wherein said control circuit stores a measure of viscosity of the working fluid in said storage device.

11. The apparatus of claim 5 further comprising an output signal generator coupled to the control circuit for generating an output signal indicative of a viscosity measurement made by the control circuit.

12. The apparatus of claim 5 wherein the control circuit identifies the special temperature by fitting measurements of the permittivity of the working fluid at a plurality of temperatures to a mathematical model of an expected curve of the variation in the permittivity over temperature, locating an inflection point in the mathematical model curve, and identifying the temperature of the inflection point as the special temperature.

13. The apparatus of claim 5 wherein the working fluid is a lubricating oil.

14. The apparatus of claim 5 wherein the working fluid is hydraulic fluid.

15. A method for analyzing a working fluid to determine the acid content of the working fluid, comprising the steps of measuring the permittivity of the working fluid while varying the temperature of the working fluid over a temperature range, the temperature range including a special temperature at which the rate of change of the permittivity over temperature is at a maximum, identifying the rate of change of the permittivity with respect to temperature at the special temperature from variation in the permittivity of the working fluid over temperature, converting the rate of change of the permittivity with respect to temperature at the special temperature to a measure of the acid content of the working fluid.

16. The method of claim 15 wherein identifying the rate of change of the permittivity with respect to temperature at the special temperature comprises fitting measurements of the permittivity of the working fluid at a plurality of temperatures to a mathematical model of an expected curve of the variation in the permittivity over temperature, and locating an inflection point in the mathematical model curve, and identifying the rate of change of the permittivity with respect to temperature at the inflection point in the mathematical model.

17. The method of claim 15 wherein the working fluid is a lubricating oil.

18. The method of claim 15 wherein the working fluid is hydraulic fluid.

19. Apparatus for analyzing a working fluid of a mechanical system to determine the acid content of the working fluid, comprising a housing, a permittivity measuring circuit including a capacitive sensor to be positioned in the working fluid, a heat transfer device associated with the sensor for varying the temperature of the working fluid over a temperature range, a temperature sensor for measuring the temperature of the working fluid, a storage device storing a plot relating acid content to the rate of change of permittivity at a special temperature, a control circuit connected to the capacitive sensor, heat transfer device, and temperature sensor, the control circuit measuring acid content of the working fluid by activating the heat transfer device to vary the temperature of the working fluid over a temperature range including a special temperature at which the rate of change of the permittivity over temperature is at a maximum, activating the permittivity measuring circuit and temperature sensor to measure the permittivity and temperature of the working fluid as temperature is varied over the range, identifying the rate of change of permittivity with respect to temperature at the special temperature from variation in the permittivity of the working fluid over temperature, and converting the value of the rate of change of permittivity with respect to temperature at the special temperature to a measure of acid content of the working fluid, based on the stored plot.

20. The apparatus of claim 19 wherein the heat transfer device is an electrical resistance heater.

21. The apparatus of claim 19 further comprising a display mounted on said housing, and a keypad mounted on said housing, wherein said capacitive sensor extends from said housing to permit immersion of said sensor in a sample of working fluid to be analyzed, and wherein said control circuit is connected to said display and keypad to prompt a user via said display to analyze a sample of working fluid, and responsive to keystrokes upon said keypad to measure the acid content of the sample of working fluid.

22. The apparatus of claim 19 wherein said housing is sized for mounting to the mechanical system, the capacitive sensor being positioned in the flow of working fluid in the mechanical system.

23. The apparatus of claim 22 wherein said housing is sized for mounting between a working fluid filter and the mechanical system.

24. The apparatus of claim 19 wherein said control circuit stores a measure of acid content of the working fluid in said storage device.

25. The apparatus of claim 19 further comprising an output signal generator coupled to the control circuit for generating an output signal indicative of a acid content measurement made by the control circuit.

26. The apparatus of claim 19 wherein the control circuit identifies the rate of change of permittivity with respect to temperature at the special temperature by fitting measurements of the permittivity of the working fluid at a plurality of temperatures to a mathematical model of an expected curve of the variation in the permittivity over temperature, locating an inflection point in the mathematical model curve, and identifying the rate of change of permittivity with respect to temperature at the inflection point.

27. The apparatus of claim 19 wherein the working fluid is a lubricating oil.

28. The apparatus of claim 19 wherein the working fluid is hydraulic fluid.

29. A method for analyzing a working fluid to determine the moisture content of the working fluid, comprising the steps of measuring the permittivity of the working fluid while varying the temperature of the working fluid over a temperature range, the temperature range including a special temperature at which the rate of change of the permittivity over temperature is at a maximum, identifying the permittivity at the special temperature from variation in the permittivity of the working fluid over temperature, converting the permittivity at the special temperature to a measure of the moisture content of the working fluid.

30. The method of claim 29 wherein identifying the permittivity at the special temperature comprises fitting measurements of the permittivity of the working fluid at a plurality of temperatures to a mathematical model of an expected curve of the variation in the permittivity over temperature, and locating an inflection point in the mathematical model curve, and identifying the permittivity at the inflection point in the mathematical model.

31. The method of claim 29 wherein the working fluid is a lubricating oil.

32. The method of claim 29 wherein the working fluid is hydraulic fluid.

33. Apparatus for analyzing a working fluid of a mechanical system to determine the moisture content of the working fluid, comprising a housing, a permittivity measuring circuit including a capacitive sensor to be positioned in the working fluid, a heat transfer device associated with the sensor for varying the temperature of the working fluid over a temperature range, a temperature sensor for measuring the temperature of the working fluid, a storage device storing a plot relating moisture content to the permittivity at a special temperature, a control circuit connected to the capacitive sensor, heat transfer device, and temperature sensor, the control circuit measuring moisture content of the working fluid by activating the heat transfer device to vary the temperature of the working fluid over a temperature range including a special temperature at which the rate of change of the permittivity over temperature is at a maximum, activating the permittivity measuring circuit and temperature sensor to measure the permittivity and temperature of the working fluid as temperature is varied over the range, identifying the permittivity at the special temperature from variation in the permittivity of the working fluid over temperature, and converting the value of permittivity at the special temperature to a measure of moisture content of the working fluid, based on the stored plot.

34. The apparatus of claim 33 wherein the heat transfer device is an electrical resistance heater.

35. The apparatus of claim 33 further comprising a display mounted on said housing, and a keypad mounted on said housing, wherein said capacitive sensor extends from said housing to permit immersion of said sensor in a sample of working fluid to be analyzed, and wherein said control circuit is connected to said display and keypad to prompt a user via said display to analyze a sample of working fluid, and responsive to keystrokes upon said keypad to measure the moisture content of the sample of working fluid.

36. The apparatus of claim 33 wherein said housing is sized for mounting to the mechanical system, the capacitive sensor being positioned in the flow of working fluid in the mechanical system.

37. The apparatus of claim 36 wherein said housing is sized for mounting between a working fluid filter and the mechanical system.

38. The apparatus of claim 33 wherein said control circuit stores a measure of moisture content of the working fluid in said storage device.

39. The apparatus of claim 33 further comprising an output signal generator coupled to the control circuit for generating an output signal indicative of a moisture content measurement made by the control circuit.

40. The apparatus of claim 33 wherein the control circuit identifies the permittivity at the special temperature by fitting measurements of the permittivity of the working fluid at a plurality of temperatures to a mathematical model of an expected curve of the variation in the permittivity over temperature, locating an inflection point in the mathematical model curve, and identifying the permittivity at the inflection point.

41. The apparatus of claim 33 wherein the working fluid is a lubricating oil.

42. The apparatus of claim 33 wherein the working fluid is hydraulic fluid.

43. A method for analyzing a working fluid to determine the density of the working fluid, comprising the steps of measuring the permittivity of the working fluid while varying the temperature of the working fluid over a temperature range, converting the rate of change of permittivity of the working fluid to a measure of the density of the working fluid.

44. The method of claim 43 further comprising fitting measurements of the permittivity of the working fluid at a plurality of temperatures to a mathematical model of an expected curve of the variation in the permittivity over temperature, and identifying the rate of change of permittivity from the mathematical model.

45. The method of claim 44 further comprising locating an inflection point in the mathematical model curve, and wherein the rate of change of permittivity is identified at a temperature not equal to the temperature of the inflection point.

46. The method of claim 45 wherein the rate of change of permittivity is identified at a temperature less than the temperature of the inflection point in the mathematical model.

47. The method of claim 43 wherein the working fluid is a lubricating oil.

48. The method of claim 43 wherein the working fluid is hydraulic fluid.

49. Apparatus for analyzing a working fluid of a mechanical system to determine the density of the working fluid, comprising a housing, a permittivity measuring circuit including a capacitive sensor to be positioned in the working fluid, a heat transfer device associated with the sensor for varying the temperature of the working fluid over a temperature range, a temperature sensor for measuring the temperature of the working fluid, a control circuit connected to the capacitive sensor, heat transfer device, and temperature sensor, the control circuit measuring density of the working fluid by activating the heat transfer device to vary the temperature of the working fluid over a temperature range, activating the permittivity measuring circuit and temperature sensor to measure the permittivity and temperature of the working fluid as temperature is varied over the range, identifying the rate of change of permittivity over temperature, and converting the rate of change of permittivity to a measure of density of the working fluid, based on an expression relating the rate of change of permittivity to density of the working fluid.

50. The apparatus of claim 49 wherein the heat transfer device is an electrical resistance heater.

51. The apparatus of claim 49 further comprising
a display mounted on said housing, and
a keypad mounted on said housing, wherein
said capacitive sensor extends from said housing to permit immersion of said sensor in a sample of working fluid to be analyzed, and
wherein said control circuit is connected to said display and keypad to prompt a user via said display to analyze a sample of working fluid, and responsive to keystrokes upon said keypad to measure the density of the sample of working fluid.

52. The apparatus of claim 49 wherein said housing is sized for mounting to the mechanical system, the capacitive sensor being positioned in the flow of working fluid in the mechanical system.

53. The apparatus of claim 52 wherein said housing is sized for mounting between a working fluid filter and the mechanical system.

54. The apparatus of claim 49 wherein said control circuit stores a measure of density of the working fluid in a storage device.

55. The apparatus of claim 49 further comprising an output signal generator coupled to the control circuit for generating an output signal indicative of a density measurement made by the control circuit.

56. The apparatus of claim 49 wherein the control circuit identifies the rate of change of permittivity by fitting measurements of the permittivity of the working fluid at a plurality of temperatures to a mathematical model of an expected curve of the variation in the permittivity over temperature, and identifying the rate of change of permittivity from the mathematical model.

57. The apparatus of claim 56 wherein the control circuit identifies the rate of change of permittivity from the mathematical model by
locating an inflection point in the mathematical model curve, and
identifying the rate of change of permittivity at a temperature not equal to the temperature of the inflection point.

58. The apparatus of claim 57 wherein the rate of change of permittivity is identified at a temperature less than the temperature of the inflection point in the mathematical model.

59. The apparatus of claim 49 wherein the working fluid is a lubricating oil.

60. The apparatus of claim 49 wherein the working fluid is hydraulic fluid.

61. A method of measuring a working fluid attribute, comprising
varying the temperature of the working fluid,
collecting measurements of working fluid permittivity while varying the temperature,
fitting the collected measurements to a mathematical model of the expected curve of the variation in permittivity over variation in temperature,
analyzing the mathematical model to measure the attribute of the working fluid.

62. The method of claim 61 wherein the temperature is varied over a range including a special temperature.

63. The method of claim 62 further comprising locating an inflection point in the mathematical model curve at the special temperature.

64. The method of claim 63 wherein the working fluid attribute is viscosity, and wherein analyzing the mathematical model comprises identifying a temperature of the inflection point in the mathematical model curve, and converting the temperature of the inflection point to a measure of viscosity of the working fluid.

65. The method of claim 63 wherein the working fluid attribute is acid content, and wherein analyzing the mathematical model comprises identifying the rate of change of the permittivity with respect to temperature at the special temperature, and converting the rate of change of permittivity with respect to temperature at the special temperature to a measure of the acid content of the working fluid.

66. The method of claim 63 wherein the working fluid attribute is moisture content, and wherein analyzing the mathematical model comprises identifying the permittivity at the special temperature, and converting the permittivity at the special temperature to a measure of the moisture content of the working fluid.

67. The method of claim 61 wherein the working fluid attribute is density, and wherein analyzing the mathematical model comprises identifying a rate of change of permittivity of the working fluid with temperature and converting the rate of change of permittivity to a measure of the density of the working fluid.

68. The method of claim 67 further comprising locating an inflection point in the mathematical model curve and identifying a rate of change of permittivity at a temperature not equal to the temperature of the inflection point.

69. The method of claim 68 wherein the rate of change of permittivity is identified at a temperature less than the temperature of the inflection point.

70. The method of claim 61 wherein the working fluid is a lubricating oil.

71. The method of claim 61 wherein the working fluid is hydraulic fluid.

72. Apparatus for analyzing a working fluid of a mechanical system to determine an attribute of the working fluid, comprising
a housing,
a parameter measuring circuit including a permittivity sensor to be positioned in communication with the working fluid,
a heat transfer device associated with the sensor for varying temperature of the working fluid,
a temperature sensor for measuring the temperature of the working fluid,
a control circuit connected to the permittivity sensor, heat transfer device, and temperature sensor, the control circuit measuring the attribute of the working fluid by
activating the heat transfer device to vary the temperature of the working fluid,
activating the temperature sensor and permittivity sensor to collect measurements of the permittivity of and temperature of the working fluid as the temperature is varied,
fitting the collected measurements to a mathematical model of the expected curve of the variation in the working fluid permittivity over variation in temperature, and
analyzing the mathematical model to measure the attribute of the working fluid.

73. The apparatus of claim 72 wherein the temperature is varied over a range including a special temperature.

74. The apparatus of claim 73 wherein said control circuit locates an inflection point in the mathematical model curve at the special temperature.

75. The apparatus of claim 74 wherein the working fluid attribute is viscosity, and wherein the control circuit analyzes the mathematical model by identifying a temperature of the inflection point in the mathematical model curve, and converting the temperature of the inflection point to a measure of viscosity of the working fluid.

76. The apparatus of claim 74 wherein the working fluid attribute is acid content, and wherein the control circuit analyzes the mathematical model by identifying the r ate of change of the permittivity with respect to temperature at inflection point, and converting the rate of change of permittivity with respect to temperature at the inflection point to a measure of the acid content of the working fluid.

77. The apparatus of claim 74 wherein the working fluid attribute is moisture content, and wherein the control circuit analyzes the mathematical model by identifying the permittivity at the inflection point, and converting the permittivity at the inflection point to a measure of the moisture content of the working fluid.

78. The apparatus of claim 72 wherein the working fluid attribute is density, and wherein the control circuit analyzes the mathematical model by identifying a rate of change of permittivity of the working fluid with temperature and converting the rate of change of permittivity to a measure of the density of the working fluid.

79. The apparatus of claim 78 wherein the control circuit analyzes the mathematical model by locating an inflection point in the mathematical model curve and identifying a rate of change of permittivity at a temperature not equal to the temperature of the inflection point.

80. The apparatus of claim 79 wherein the control circuit identifies the rate of change of permittivity at a temperature less than the temperature of the inflection point.

81. The apparatus of claim 72 wherein the heat transfer device is an electrical resistance heater.

82. The apparatus of claim 72 further comprising
   a display mounted on said housing, and
   a keypad mounted on said housing, wherein
      said permittivity sensor extends from said housing to permit immersion of said sensor in a sample of working fluid to be analyzed, and
      wherein said control circuit is connected to said display and keypad to prompt a user via said display to analyze a sample of working fluid, and responsive to keystrokes upon said keypad to measure the attribute of the sample of working fluid.

83. The apparatus of claim 72 wherein said housing is sized for mounting to the mechanical system, the permittivity sensor being positioned in the flow of working fluid in the mechanical system.

84. The apparatus of claim 83 wherein said housing is sized for mounting between a working fluid filter and the mechanical system.

85. The apparatus of claim 72 further comprising an output signal generator coupled to the control circuit for generating an output signal indicative of an attribute measurement made by the control circuit.

86. The apparatus of claim 72 wherein the working fluid is a lubricating oil.

87. The apparatus of claim 72 wherein the working fluid is hydraulic fluid.

88. A method for analyzing a fluid to determine an attribute of the fluid, comprising the steps of
   generating a dielectric relaxation spectrum for the fluid by measuring the permittivity of the fluid while varying over a range an environmental variable affecting the permittivity of the fluid, the range including a special point at which the rate of change of the permittivity with the environmental variable is at a maximum,
   identifying the special point in the dielectric relaxation spectrum from variation in the permittivity of the fluid,
   converting features of the dielectric relaxation spectrum at the special point to a measure of the attribute of the fluid.

89. The method of claim 88 wherein the environmental variable is frequency of applied electrical stimulation.

90. The method of claim 88 wherein the environmental variable is temperature.

91. The method of claim 90 wherein the fluid attribute is viscosity.

92. The method of claim 90 wherein the fluid attribute is acid content.

93. The method of claim 90 wherein the fluid parameter is moisture content.

94. The method of claim 90 wherein identifying the special point comprises
   fitting measurements of the permittivity of the fluid at a plurality of temperatures to a mathematical model of an expected curve of the variation in the permittivity over temperature, and
   locating an inflection point in the mathematical model curve, and
   identifying the inflection point as the special point.

95. The method of claim 88 wherein the fluid is a lubricating oil.

96. The method of claim 88 wherein the fluid is hydraulic fluid.

97. Apparatus for analyzing a fluid to determine an attribute of the fluid, comprising the steps of
   a housing,
   a permittivity measuring circuit to be positioned in communication with the fluid,
   an environmental variable control device associated with the sensor for varying an environmental variable affecting the fluid,
   an environmental variable sensor for measuring the environmental variable affecting the fluid,
   a control circuit connected to the parameter sensor, environmental variable control device, and environmental variable sensor, the control circuit determining the attribute of the fluid by
      activating the environmental variable control device to vary the environmental variable affecting the fluid,
      activating the environmental variable sensor and permittivity measuring circuit to collect a dielectric relaxation spectrum of measurements of the permittivity and environmental variable affecting the fluid as the environmental variable is varied over a range, the range including a special point at which the rate of change of the permittivity with the environmental variable is at a maximum,
      identifying the special point in the dielectric relaxation spectrum from variation in the permittivity of the fluid, and
      converting features of the dielectric relaxation spectrum at the special point to a measure of the attribute of the fluid.

98. The apparatus of claim 97 wherein the environmental variable is frequency of applied electrical stimulation.

99. The apparatus of claim 97 wherein the environmental variable is temperature.

100. The apparatus of claim 99 wherein the fluid attribute is viscosity.

101. The apparatus of claim 99 wherein the fluid attribute is acid content.

102. The apparatus of claim 99 wherein the fluid parameter is moisture content.

103. The apparatus of claim 99 wherein the control circuit identifies the special point by fitting measurements of the permittivity of the fluid at a plurality of temperatures to a mathematical model of an expected curve of the variation in the permittivity over temperature, locating an inflection point in the mathematical model curve, and identifying the inflection point as the special point.

104. The apparatus of claim 97 wherein the fluid is a lubricating oil.

105. The apparatus of claim 97 wherein the fluid is hydraulic fluid.

* * * * *